(12) United States Patent
Tanaka et al.

(10) Patent No.: US 11,077,167 B2
(45) Date of Patent: Aug. 3, 2021

(54) AGENT FOR PROMOTING SKELETAL MUSCLE INJURY REPAIR

(71) Applicant: Osaka University, Osaka (JP)

(72) Inventors: Susumu Tanaka, Osaka (JP); Mikihiko Kogo, Osaka (JP); Hirofumi Yamamoto, Osaka (JP); Naomasa Kawaguchi, Osaka (JP); Yoshinosuke Hamada, Osaka (JP)

(73) Assignee: OSAKA UNIVERSITY, Osaka (JP)

( * ) Notice: Subject to any disclaimer, the term of this patent is extended or adjusted under 35 U.S.C. 154(b) by 0 days.

(21) Appl. No.: 16/619,879

(22) PCT Filed: Jun. 12, 2018

(86) PCT No.: PCT/JP2018/022329
§ 371 (c)(1),
(2) Date: Dec. 5, 2019

(87) PCT Pub. No.: WO2018/230535
PCT Pub. Date: Dec. 20, 2018

(65) Prior Publication Data
US 2020/0206300 A1  Jul. 2, 2020

(30) Foreign Application Priority Data

Jun. 15, 2017  (JP) .............................. JP2017-117759
Nov. 29, 2017  (JP) .............................. JP2017-229688

(51) Int. Cl.
A61K 38/08     (2019.01)
A61P 21/00     (2006.01)
A61K 38/39     (2006.01)

(52) U.S. Cl.
CPC .............. *A61K 38/08* (2013.01); *A61K 38/39* (2013.01); *A61P 21/00* (2018.01)

(58) Field of Classification Search
CPC ........ A61K 38/08; A61K 38/19; A61K 38/39; A61P 21/00; A61P 43/00; C07K 14/52; C07K 7/06
See application file for complete search history.

(56) References Cited

U.S. PATENT DOCUMENTS

2004/0266696 A1  12/2004  Nokihara et al.
2011/0245187 A1  10/2011  Hamada et al.

FOREIGN PATENT DOCUMENTS

WO  WO 03/030925 A1    4/2003
WO  WO 2008/026634 A1  3/2008
WO  WO 2012/172887 A1  12/2012
WO  WO 2016/084935 A1  6/2016

OTHER PUBLICATIONS

Translation to English of WO2012172887, accessed online at https://patents.google.com/patent/JPWO2012172887A1/en?oq=wo2012172887 on Nov. 5, 2020. 30 pages. (Year: 2012).*
Hamada, Yoshinosuke et al., "Angiogenic activity of osteopontin-derived peptide SVVYGLR" Biochemical and Biophysical Research Communications, 2003, pp. 153-157, vol. 310.
Hamada, Yoshinosuke et al., "Osteopontin-derived Peptide SVVYGLR Induces Angiogenesis In Vivo" Dental Materials Journal, 2004, pp. 650-655, vol. 23, No. 4.
Liu, Huijie et al., "β-Integrin mediates satellite cell differentiation in regenerating mouse muscle" The FASEB Journal, 2011, pp. 1914-1921, vol. 25.
Maeda, Yasushi et al., "CXCL12 and osteopontin from bone marrow-derived mesenchymal stromal cells improve muscle regeneration" Scientific Reports, Jun. 2017, vol. 7, No. 1.
Pagel, Charles N. et al., "Osteopontin, inflammation and myogenesis: influencing regeneration, fibrosis and size of skeletal muscle" Journal of Cell Communication and Signaling, 2014, pp. 95-103, vol. 8, No. 2.
Uaesoontrachoon, Kitipong et al., "Osteopontin and skeletal muscle myoblasts: Association with muscle regeneration and regulation of myoblast function in vitro" The International Journal of Biochemistry & Cell Biology, 2008, pp. 2303-2314, vol. 40.
Uchinaka, Ayako et al., "Transplantation of myoblast sheets that secrete the novel peptide SVVYGLR improves cardiac function in failing hearts" Cardiovascular Research, 2013, pp. 102-110, vol. 99.
Uchinaka, Ayako et al., "SVVYGLR motif of the thrombin-cleaved N-terminal osteopontin fragment enhances the synthesis of collagen type III in myocardial fibrosis" Mol Cell Biochem, 2015, pp. 191-203, vol. 408.
International Search Report for PCT/JP2018/022329 dated Aug. 2, 2018.
International Preliminary Report on Patentability for PCT/JP2018/022329 dated Aug. 14, 2018.

* cited by examiner

*Primary Examiner* — Marcela M Cordero Garcia
(74) *Attorney, Agent, or Firm* — Knobbe Martens Olson & Bear, LLP

(57) ABSTRACT

The present invention provides an agent for promoting skeletal muscle injury repair which agent comprises at least one peptide selected from the following (1) to (4):

(1) a peptide consisting of the amino acid sequence of SEQ ID NO: 1,
(2) a peptide consisting of the amino acid sequence of SEQ ID NO: 2,
(3) a peptide consisting of the amino acid sequence of SEQ ID NO: 3, and
(4) a peptide which is a human osteopontin fragment and has the amino acid sequence of SEQ ID NO: 1, 2, or 3 at the C-terminus, or a salt thereof as an active ingredient.

6 Claims, 14 Drawing Sheets
Specification includes a Sequence Listing.

Lissajous pattern EMG (grinding phase)

Number of blood vessels per field of view (A) HE-staining image

Arrow: immature muscle fiber with central nuclei (B) Number of muscle fibers with central nuclei per field of view (A) Immunostaining image (for myogenin)

Arrow: muscle fiber (myotube cell) with dark-stained nuclei (B) Number of myogenin-positive nuclei per field of view SV side    Control side

SEQUENCE LISTING

<160> NUMBER OF SEQ ID NOS: 6

<210> SEQ ID NO 1
<211> LENGTH: 7
<212> TYPE: PRT
<213> ORGANISM: Artificial
<220> FEATURE:
<223> OTHER INFORMATION: synthesized peptide

<400> SEQUENCE: 1

Ser Val Val Tyr Gly Leu Arg
1               5

<210> SEQ ID NO 2
<211> LENGTH: 6

```
<212> TYPE: PRT
<213> ORGANISM: Artificial
<220> FEATURE:
<223> OTHER INFORMATION: synthesized peptide

<400> SEQUENCE: 2

Ser Val Val Tyr Gly Leu
1               5

<210> SEQ ID NO 3
<211> LENGTH: 6
<212> TYPE: PRT
<213> ORGANISM: Artificial
<220> FEATURE:
<223> OTHER INFORMATION: synthesized peptide

<400> SEQUENCE: 3

Val Val Tyr Gly Leu Arg
1               5

<210> SEQ ID NO 4
<211> LENGTH: 314
<212> TYPE: PRT
<213> ORGANISM: Homo sapiens

<400> SEQUENCE: 4

Met Arg Ile Ala Val Ile Cys Phe Cys Leu Leu Gly Ile Thr Cys Ala
1               5                   10                  15

Ile Pro Val Lys Gln Ala Asp Ser Gly Ser Ser Glu Glu Lys Gln Leu
                20                  25                  30

Tyr Asn Lys Tyr Pro Asp Ala Val Ala Thr Trp Leu Asn Pro Asp Pro
            35                  40                  45

Ser Gln Lys Gln Asn Leu Leu Ala Pro Gln Asn Ala Val Ser Ser Glu
        50                  55                  60

Glu Thr Asn Asp Phe Lys Gln Glu Thr Leu Pro Ser Lys Ser Asn Glu
65                  70                  75                  80

Ser His Asp His Met Asp Asp Met Asp Asp Glu Asp Asp Asp Asp His
                85                  90                  95

Val Asp Ser Gln Asp Ser Ile Asp Ser Asn Asp Ser Asp Asp Val Asp
                100                 105                 110

Asp Thr Asp Asp Ser His Gln Ser Asp Glu Ser His His Ser Asp Glu
            115                 120                 125

Ser Asp Glu Leu Val Thr Asp Phe Pro Thr Asp Leu Pro Ala Thr Glu
        130                 135                 140

Val Phe Thr Pro Val Val Pro Thr Val Asp Thr Tyr Asp Gly Arg Gly
145                 150                 155                 160

Asp Ser Val Val Tyr Gly Leu Arg Ser Lys Ser Lys Lys Phe Arg Arg
                165                 170                 175

Pro Asp Ile Gln Tyr Pro Asp Ala Thr Asp Glu Asp Ile Thr Ser His
            180                 185                 190

Met Glu Ser Glu Glu Leu Asn Gly Ala Tyr Lys Ala Ile Pro Val Ala
        195                 200                 205

Gln Asp Leu Asn Ala Pro Ser Asp Trp Asp Ser Arg Gly Lys Asp Ser
    210                 215                 220

Tyr Glu Thr Ser Gln Leu Asp Asp Gln Ser Ala Glu Thr His Ser His
225                 230                 235                 240

Lys Gln Ser Arg Leu Tyr Lys Arg Lys Ala Asn Asp Glu Ser Asn Glu
                245                 250                 255
```

-continued

```
His Ser Asp Val Ile Asp Ser Gln Glu Leu Ser Lys Val Ser Arg Glu
            260                 265                 270

Phe His Ser His Glu Phe His Ser His Glu Asp Met Leu Val Val Asp
        275                 280                 285

Pro Lys Ser Lys Glu Glu Asp Lys His Leu Lys Phe Arg Ile Ser His
        290                 295                 300

Glu Leu Asp Ser Ala Ser Ser Glu Val Asn
305                 310

<210> SEQ ID NO 5
<211> LENGTH: 168
<212> TYPE: PRT
<213> ORGANISM: Homo sapiens

<400> SEQUENCE: 5

Met Arg Ile Ala Val Ile Cys Phe Cys Leu Leu Gly Ile Thr Cys Ala
1               5                   10                  15

Ile Pro Val Lys Gln Ala Asp Ser Gly Ser Ser Glu Glu Lys Gln Leu
            20                  25                  30

Tyr Asn Lys Tyr Pro Asp Ala Val Ala Thr Trp Leu Asn Pro Asp Pro
        35                  40                  45

Ser Gln Lys Gln Asn Leu Leu Ala Pro Gln Asn Ala Val Ser Ser Glu
    50                  55                  60

Glu Thr Asn Asp Phe Lys Gln Glu Thr Leu Pro Ser Lys Ser Asn Glu
65                  70                  75                  80

Ser His Asp His Met Asp Asp Met Asp Glu Asp Asp Asp His
                85                  90                  95

Val Asp Ser Gln Asp Ser Ile Asp Ser Asn Asp Ser Asp Asp Val Asp
            100                 105                 110

Asp Thr Asp Asp Ser His Gln Ser Asp Glu Ser His His Ser Asp Glu
        115                 120                 125

Ser Asp Glu Leu Val Thr Asp Phe Pro Thr Asp Leu Pro Ala Thr Glu
    130                 135                 140

Val Phe Thr Pro Val Val Pro Thr Val Asp Thr Tyr Asp Gly Arg Gly
145                 150                 155                 160

Asp Ser Val Val Tyr Gly Leu Arg
                165

<210> SEQ ID NO 6
<211> LENGTH: 7
<212> TYPE: PRT
<213> ORGANISM: Artificial
<220> FEATURE:
<223> OTHER INFORMATION: synthesized peptide

<400> SEQUENCE: 6

Gly Tyr Arg Val Leu Ser Val
1               5
```

AGENT FOR PROMOTING SKELETAL MUSCLE INJURY REPAIR

CROSS REFERENCE TO RELATED APPLICATIONS

This application is a U.S. National Phase Application of PCT International Application Number PCT/JP2018/022329, filed on Jun. 12, 2018, designating the United States of America and published in the Japanese language, which is an International Application of and claims the benefit of priority to Japanese Patent Application No. 2017-117759, filed on Jun. 15, 2017, and Japanese Patent Application No. 2017-229688, filed on Nov. 29, 2017. The disclosures of the above-referenced applications are hereby expressly incorporated by reference in their entireties.

REFERENCE TO SEQUENCE LISTING

A Sequence Listing submitted as an ASCII text file via EFS-Web is hereby incorporated by reference in accordance with 37 U.S.C. § 1.52(e). The name of the ASCII text file for the Sequence Listing is SeqList-IWAT007-008APC.txt, the date of creation of the ASCII text file is Nov. 20, 2019, and the size of the ASCII text file is 6 KB.

TECHNICAL FIELD

The present invention relates to an agent for promoting skeletal muscle injury repair.

BACKGROUND ART

Skeletal muscle is a striated muscle like myocardial muscle but is different from myocardial muscle in that a large number of progenitor cells called satellite cells are present inside. After muscle injury, satellite cells participate in tissue repair and regeneration, and the injured muscle is almost entirely healed without functional defects. When muscle fibers have torn, satellite cells residing on the basement membrane of muscle fibers become activated to proliferate and differentiate into myoblasts at the muscle injury site. Myoblasts fuse to each other to form multinucleated cells (myotube cells). The cells further fuse together to fill a gap in injured muscle fibers, re-establish the continuity of muscle fibers, and form mature muscle fibers in about one month.

Skeletal muscle can be said to be a tissue with a high self-repair capability due to the presence of satellite cells. However, the number and quality of satellite cells are known to decline with aging, and in consideration of this fact, muscle functional loss is never a rare pathological condition in the recent super-aged society. In addition, branchial arch muscle reportedly has a smaller number of satellite cells, and surgery of the head and neck region often entails postoperative muscle functional loss.

In recent years, novel tissue regenerative therapies using cytokines and angiogenic factors have been studied. However, growth factors conventionally used for research and therapy, such as VEGF (vascular endothelial growth factor), HGF (hepatocyte growth factor), and bFGF (basic fibroblast growth factor), are extracted or recombinant proteins of hundreds of amino acids and may potentially cause unanticipated adverse effects or infections. As compared with such growth factors, peptides of about 10 amino acids are less likely to cause adverse effects due to their lower antigenicity, safer for use, and more readily metabolized. In addition, such peptides are simpler in design and can be reliably obtained by established highly efficient synthesis methods and analytical tests. Therefore, such peptides are advantageous over the growth factors mentioned above.

The present inventors have found that a 7-amino-acid peptide (SVVYGLR: SEQ ID NO: 1) which represents part of osteopontin (OPN), an extracellular matrix protein (this peptide is hereinafter referred to as "SV peptide") has a high angiogenic activity that is comparable to that of VEGF, an major angiogenic factor (Patent Literature 1, Non Patent Literature 1, Non Patent Literature 2). In addition, the present inventors have found that the SV peptide promotes mesenchymal cell proliferation (Patent Literature 2), improves cardiac function (Patent Literature 3), and promotes type III collagen production in fibroblasts (Patent Literature 4). However, it is yet unknown that the SV peptide promotes skeletal muscle injury repair.

CITATION LIST

Patent Literature

Patent Literature 1: WO 2003/030925
Patent Literature 2: WO 2008/026634
Patent Literature 3: WO 2012/172887
Patent Literature 4: WO 2016/084935

Non Patent Literature

Non Patent Literature 1:
Hamada Y, Norihara Y, Okazaki M, Fujitani W, Matsumoto T, Matsuura N and Takahashi J. Angiogenic activity of osteopontin-derived peptide SVVYGLR. Biochem Biophys Res Commun 2003; 310: 153-157.
Non Patent Literature 2:
Hamada Y, Yuki K, Okazaki M, Fujitani W, Matsumoto T, Hashida K, Kobashi M, Matsuura N and Takahashi J. Osteopontin-derived peptide SVVYGLR induces angiogenesis in vivo. Dent Mater J 2004; 23:650-655.

SUMMARY OF INVENTION

Technical Problem

An object of the present invention is to provide an agent for promoting skeletal muscle injury repair.

Solution to Problem

The present invention includes the following to achieve the above-mentioned object.
[1] An agent for promoting skeletal muscle injury repair, the agent comprising at least one peptide selected from the following (1) to (4):
(1) a peptide consisting of the amino acid sequence of SEQ ID NO: 1,
(2) a peptide consisting of the amino acid sequence of SEQ ID NO: 2,
(3) a peptide consisting of the amino acid sequence of SEQ ID NO: 3, and
(4) a peptide which is a human osteopontin fragment and has the amino acid sequence of SEQ ID NO: 1, 2, or 3 at the C-terminus, or a salt thereof as an active ingredient.
[2] The agent for promoting skeletal muscle injury repair according to the above [1], wherein the agent is capable of promoting satellite cell activation and/or differentiation.

[3] The agent for promoting skeletal muscle injury repair according to the above [1] or [2], wherein the skeletal muscle injury is muscle rupture, muscle atrophy, or muscle degeneration.

[4] The agent for promoting skeletal muscle injury repair according to any of the above [1] to [3], wherein the agent is capable of reducing scar formation at a skeletal muscle injury site.

[5] An agent for promoting satellite cell activation at a skeletal muscle injury site, the agent comprising at least one peptide selected from the following (1) to (4):
(1) a peptide consisting of the amino acid sequence of SEQ ID NO: 1,
(2) a peptide consisting of the amino acid sequence of SEQ ID NO: 2,
(3) a peptide consisting of the amino acid sequence of SEQ ID NO: 3, and
(4) a peptide which is a human osteopontin fragment and has the amino acid sequence of SEQ ID NO: 1, 2, or 3 at the C-terminus, or a salt thereof as an active ingredient.

[6] An agent for promoting satellite cell differentiation at a skeletal muscle injury site, the agent comprising at least one peptide selected from the following (1) to (4):
(1) a peptide consisting of the amino acid sequence of SEQ ID NO: 1,
(2) a peptide consisting of the amino acid sequence of SEQ ID NO: 2,
(3) a peptide consisting of the amino acid sequence of SEQ ID NO: 3, and
(4) a peptide which is a human osteopontin fragment and has the amino acid sequence of SEQ ID NO: 1, 2, or 3 at the C-terminus, or a salt thereof as an active ingredient.

[7] An agent for reducing scar formation at a skeletal muscle injury site, the agent comprising at least one peptide selected from the following (1) to (4):
(1) a peptide consisting of the amino acid sequence of SEQ ID NO: 1,
(2) a peptide consisting of the amino acid sequence of SEQ ID NO: 2,
(3) a peptide consisting of the amino acid sequence of SEQ ID NO: 3, and
(4) a peptide which is a human osteopontin fragment and has the amino acid sequence of SEQ ID NO: 1, 2, or 3 at the C-terminus, or a salt thereof as an active ingredient.

Advantageous Effects of Invention

The present invention provides an agent for promoting skeletal muscle injury repair. The agent of the present invention for promoting skeletal muscle injury repair can promote activation and/or differentiation of satellite cells at a skeletal muscle injury site, and therefore, enables repair of surgical or traumatic injury in skeletal muscle in a shorter time than the time for spontaneous recovery.

BRIEF DESCRIPTION OF DRAWINGS

FIG. 2A is a graph showing feeding efficiency (the food intake per unit of mastication time), and FIG. 2B is a graph showing body weight change.

FIG. 5A is an HE-staining image, and FIG. 5B is a graph showing the number of muscle fibers with central nuclei on the SV side or the non-administration (control) side.

FIG. 6A is a sirius red-staining image of the SV peptide side, FIG. 6B is a sirius red-staining image of the control side, and FIG. 6C is a graph showing the granulation tissue area on the SV side or the non-administration (control) side.

FIG. 7A is an immunostaining image for myogenin, and FIG. 7B is a graph showing the number of myogenin-positive nuclei on the SV side or the non-administration (control) side.

FIG. 12A shows the results for the SV group, and FIG. 12B shows the results for the PBS group.

FIG. 13A presents sirius red-staining images in the SV group and in the PBS group. FIG. 13B shows the amount of scar formation on the cut surfaces (dashed line in the figure) measured using an image-analysis software.

FIG. 15A is an image of a sirius-red staining specimen on the SV peptide administration side (SV side), and FIG. 15B is an image of a sirius-red staining specimen on the non-administration (control) side.

FIG. 16A shows the results for human skeletal muscle satellite cells, and FIG. 16B shows the results for human skeletal muscle myoblasts.

FIG. 17A shows the results for human skeletal muscle satellite cells, and FIG. 17B shows the results for human skeletal muscle myoblasts.

DESCRIPTION OF EMBODIMENTS

Figure 1:
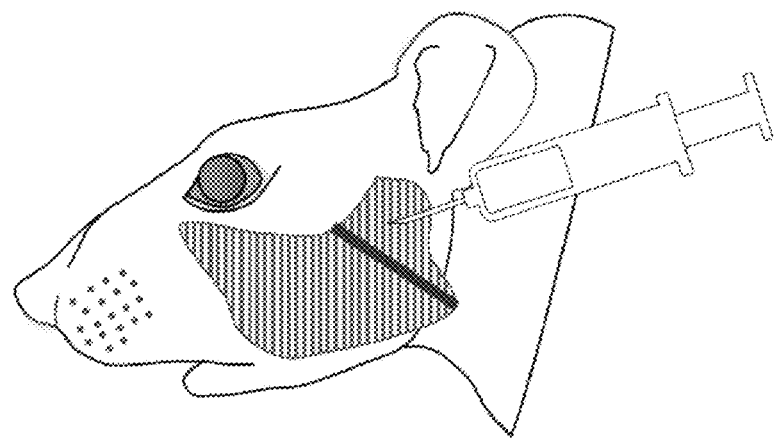
FIG. 1 illustrates the site of the incision made in the masseter muscle in a muscle injury model rat.

The present invention provides an agent for promoting skeletal muscle injury repair, the agent comprising at least one peptide selected from the following (1) to (4):
(1) a peptide consisting of the amino acid sequence of SEQ ID NO: 1,
(2) a peptide consisting of the amino acid sequence of SEQ ID NO: 2,
(3) a peptide consisting of the amino acid sequence of SEQ ID NO: 3, and
(4) a peptide which is a human osteopontin fragment and has the amino acid sequence of SEQ ID NO: 1, 2, or 3 at the C-terminus, or a salt thereof as an active ingredient.

The amino acid sequences of SEQ ID NOs: 1 to 3 are as follows.

```
SEQ ID NO: 1:
SVVYGLR

SEQ ID NO: 2:
SVVYGL

SEQ ID NO: 3:
VVYGLR
```

The present inventors have confirmed that a peptide SVVYGL (SEQ ID NO: 2), namely a peptide lacking the C-terminal R residue of SVVYGLR (SEQ ID NO: 1), and a peptide VVYGLR (SEQ ID NO: 3), namely a peptide lacking the N-terminal S residue of SVVYGLR (SEQ ID NO: 1), retain the angiogenic activity of SVVYGLR (SEQ ID NO: 1). In addition, the present inventors have confirmed that an osteopontin fragment having SVVYGLR (SEQ ID NO: 1) at the C-terminus is comparable to SVVYGLR (SEQ ID NO: 1) in the ability of promoting type III collagen production in fibroblasts (see Patent Literature 4). From these findings, it can be reasonably inferred that all the peptides of the above (1) to (4) promote skeletal muscle injury repair.

The amino acid sequence of human osteopontin is, for example, the amino acid sequence of SEQ ID NO: 4. Human osteopontin is known to contain SVVYGLR (SEQ ID NO: 1) and to have a thrombin cleavage site just downstream of SVVYGLR (SEQ ID NO: 1). For example, thrombin cleavage of a human osteopontin consisting of the amino acid sequence of SEQ ID NO: 4 gives rise to a fragment consisting of the amino acid sequence of SEQ ID NO: 5, in other words, a peptide which is a human osteopontin fragment and has the amino acid sequence of SEQ ID NO: 1 at the C-terminus.

Examples of the amino acid sequence of human osteopontin also include an amino acid sequence that is identical to the amino acid sequence of SEQ ID NO: 4 except for having deletion, substitution, or addition of one to several amino acids; and an amino acid sequence having at least 80% identity to the amino acid sequence of SEQ ID NO: 4. As used herein, the "amino acid sequence having deletion, substitution, or addition of one to several amino acids" means deletion, substitution, or addition of an amino acid(s) of which the number substantially corresponds to the number of amino acids that can be deleted, substituted or added by a known method for preparing mutant peptides, such as site-directed mutagenesis (preferably 10 or less amino acids, more preferably 7 or less amino acids, and even more preferably 5 amino acids, 4 amino acids, 3 amino acids, 2 amino acids, or 1 amino acid). The "amino acid sequence having at least 80% identity" is, for example, an amino acid sequence having at least 85%, 90%, 92%, 95%, 96%, 97%, 98%, or 99% identity. A protein that is equivalent in structure and function to the native human osteopontin can be called "human osteopontin", and the amino acid sequence of the protein is the "amino acid sequence of human osteopontin".

The length of the human osteopontin fragment is not particularly limited, but the total number of amino acid residues in the human osteopontin fragment is preferably about 170 or less, more preferably about 150 or less, and still more preferably about 100 or less. Moreover, in view of ease of handling, production efficiency, and the risk of adverse reactions such as antigenicity, the total number of amino acid residues in the human osteopontin fragment is preferably about 50 or less, more preferably about 30 or less, still more preferably about 20 or less, and particularly preferably about 10 or less.

The peptide used as the active ingredient of the agent of the present invention for promoting skeletal muscle injury repair may have one or more amino acids of which the side chain is modified by a substituent. The substituent is not particularly limited, and examples include a fluorine atom, a chlorine atom, a cyano group, a hydroxyl group, a nitro group, an alkyl group, a cycloalkyl group, an alkoxy group, and an amino group. Preferably, the benzene ring of tryptophan or phenylalanine is modified by a substituent.

The peptide used as the active ingredient of the agent of the present invention for promoting skeletal muscle injury repair may have a carboxyl group (—COOH), a carboxylate (—COO—), an amide (—CONH$_2$) or an ester (—COOR) at the C-terminus. Examples of the R moiety in the ester include $C_{1-6}$ alkyl groups such as methyl, ethyl, n-propyl, isopropyl, and n-butyl; $C_{3-8}$ cycloalkyl groups such as cyclopentyl and cyclohexyl; $C_{6-12}$ aryl groups such as phenyl and α-naphthyl; and $C_{7-14}$ aralkyl groups such as phenyl-$C_{1-2}$ alkyl groups including benzyl and phenethyl, and α-naphthyl-$C_{1-2}$ alkyl groups including α-naphthylmethyl. Also included is a pivaloyloxymethyl group, which is widely used in an ester for oral use. Examples of the amide moiety include amides; amides substituted with one or two $C_{1-6}$ alkyl groups; amides substituted with one or two $C_{1-6}$ alkyl groups substituted with a phenyl group; and amides in which a 5- to 7-membered azacyclo alkane containing the nitrogen atom of the amide group is formed. When the peptide of the present invention has a carboxyl group or a carboxylate group at a site other than the C-terminus, these groups may be amidated or esterified. Such modified peptides are encompassed in the scope of the peptide of the present invention.

In the peptide used as the active ingredient of the agent of the present invention for promoting skeletal muscle injury repair, the N-terminal amino group may be protected by a protecting group (e.g., $C_{1-6}$ acyl groups including a formyl group and a $C_{2-6}$ alkanoyl group such as acetyl, etc.). In said peptide, the substituent in the side chain of an intramolecular amino acid may be protected by an appropriate protecting group (e.g., $C_{1-6}$ acyl groups including a formyl group and a $C_{2-6}$ alkanoyl group such as acetyl, etc.). Such modified peptides are encompassed in the scope of the peptide of the present invention.

The peptide used as the active ingredient of the agent of the present invention for promoting skeletal muscle injury repair may be in the form of a salt, and the salt is preferably a pharmaceutically acceptable salt. Examples of the pharmaceutically acceptable salt include salts with acids such as hydrochloric acid, sulfuric acid, phosphoric acid, lactic acid, tartaric acid, maleic acid, fumaric acid, oxalic acid, malic acid, citric acid, oleic acid, palmitic acid, etc.; salts with alkali metals such as sodium and potassium, salts with alkaline earth metals such as calcium, and salts with aluminum hydroxide or carbonate; and salts with triethylamine, benzylamine, diethanolamine, t-butylamine, dicyclohexylamine, arginine, etc.

The peptide used as the active ingredient of the agent of the present invention for promoting skeletal muscle injury repair or a salt thereof can be produced by a solid phase synthesis method (e.g., the Fmoc method and the Boc method) or a liquid phase synthesis method according to a known ordinary peptide synthesis protocol. Alternatively, a transformant with an expression vector containing a DNA encoding the peptide can be used to produce the peptide. Alternatively, the peptide can be produced by in vitro coupled transcription-translation system.

Examples of the skeletal muscle injury of which the repair is promoted by the agent of the present invention for promoting skeletal muscle injury repair include muscle rupture, muscle atrophy, and muscle degeneration. Specific examples include muscle rupture caused by surgery; muscle rupture caused by trauma such as fracture, bruise, and muscle strain; disuse muscle atrophy caused by reduction in number of motor units due to long-term jaw closure after head-and-neck surgery; muscular atrophy caused by cancer cachexia; muscular atrophy caused by sarcopenia and/or aging; progressive muscular atrophy in hereditary neuromuscular disease such as muscular dystrophy; fibrosis and scar contracture after extended surgical myectomy; scar contracture accompanied by motor dysfunction after plastic surgery for congenital abnormal muscle morphology such as cleft palate; muscle degeneration due to reduced regenerative capacity caused by sarcopenia and/or aging; etc.

The agent of the present invention for promoting skeletal muscle injury repair is very useful for disuse muscle atrophy caused by long-term bed rest etc. because the agent promotes muscle regeneration and repair and helps early recovery of motor function. The agent of the present invention is also effective for functional improvement of congenital diseases with abnormal muscle morphology and/or function (cleft palate etc.), in particular, functional improvement in cases in which conventional surgery or therapy alone is insufficient to restore muscle function. In addition, the agent of the present invention is effective for functional improvement and medical condition improvement of acquired intractable neuromuscular diseases (muscular dystrophy etc.). Moreover, the agent of the present invention is potentially effective in inhibiting the progression of muscular atrophy and degeneration caused by aging or sarcopenia and in preventing cognitive impairment due to ADL (Activities of Daily Living) decline.

The agent of the present invention for promoting skeletal muscle injury repair has shown to be capable of reducing scar formation at a skeletal muscle injury site. Therefore, the agent of the present invention for promoting skeletal muscle injury repair can be referred to as an "agent for reducing scar formation at a skeletal muscle injury site". Examples of the skeletal muscle injury in which scar formation is reduced by the agent of the present invention include muscle rupture and muscle degeneration, examples of which are described above.

Skeletal muscle is composed of multinucleated muscle fibers (myocytes), and a large number of satellite cells are present on the basement membrane of each muscle fiber. Satellite cells are usually be quiescent, but become activated in response to signals generated due to muscle injury etc. Activated satellite cells proliferate and differentiate into myoblasts. Satellite cells originally have pluripotency, but after activation-induced upregulation of MyoD gene expression, the cells become destined to differentiate into myoblasts. Concomitantly, the expression of a myogenin gene, which is downstream of the MyoD gene and involved in myoblast differentiation into myotube cells and maintenance of the myotube cells, is induced, resulting in mature myocyte formation. The agent of the present invention for promoting skeletal muscle injury repair is capable of promoting satellite cell activation and/or differentiation at a skeletal muscle injury site. Therefore, the agent of the present invention for promoting skeletal muscle injury repair can be called an "agent for promoting satellite cell activation at a skeletal muscle injury site" or an "agent for promoting satellite cell differentiation at a skeletal muscle injury site".

In an embodiment, the agent of the present invention for promoting skeletal muscle injury repair can be used as a medicament for repairing a skeletal muscle injury site. In this embodiment, the agent of the present invention for promoting skeletal muscle injury repair and optionally a pharmaceutically acceptable carrier or additive can be blended and formulated into a dosage form. Specific examples of the dosage form include oral preparations such as tablets, coated tablets, pills, powders, granules, capsules, solutions, suspensions, and emulsions; and parenteral preparations such as injections, infusions, suppositories, ointments, and patches. The amount of the carrier or the additive to be used is determined as appropriate based on the range of amount conventionally used in the pharmaceutical field. The carrier or the additive that can be used is not particularly limited, and examples include various carriers such as water, physiological saline, other aqueous solvents, and aqueous or oily bases; and various additives such as excipients, binders, pH adjusters, disintegrants, absorption enhancers, lubricants, colorants, corrigents, and fragrances.

Examples of the additive that can be blended into tablets, capsules, and the like include binders such as gelatin, cornstarch, tragacanth, and gum arabic; fillers such as crystalline cellulose; bulking agents such as cornstarch, gelatin, and alginic acid; lubricants such as magnesium stearate; sweeteners such as sucrose, lactose, and saccharin; and flavors such as peppermint, Gaultheria adenothrix oil, and cherry. In the case where the unit dosage form is a capsule, a liquid carrier such as fats and oils can be further contained in addition to the above-mentioned ingredients. A sterile composition for injection can be prepared according to the usual pharmaceutical formulation practice, for example, by dissolving or suspending an active substance in a vehicle such as water for injection and a natural vegetable oil such as sesame oil and coconut oil. As an aqueous liquid for injection, for example, physiological saline, an isotonic solution containing glucose and an auxiliary substance (e.g., D-sorbitol, D-mannitol, sodium chloride, etc.), or the like can be used, optionally together with a suitable solubilizer such as alcohols (e.g., ethanol etc.), polyalcohols (e.g., propylene glycol, polyethylene glycol, etc.), and nonionic surfactants (e.g., polysorbate 80™, HCO-50, etc.). As an oily liquid, for example, sesame oil, soybean oil, or the like can be used, optionally together with a solubilizer such as benzyl benzoate and benzyl alcohol. Further, a buffering agent (e.g., phosphate buffer, sodium acetate buffer, etc.), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, and/or the like may also be added.

In an embodiment, the agent of the present invention for promoting skeletal muscle injury repair may be used as an injection for direct administration into a muscle in the surrounding area of skeletal muscle injury, or as an ointment or patch for application or attachment to a muscle in the surrounding area of skeletal muscle injury. In addition, the agent of the present invention for promoting skeletal muscle injury repair may be in a form in which the active ingredient peptide is conjugated to a carrier. The carrier is not particularly limited, and examples include resins for use in artificial organs etc., and biopolymers such as proteins. In a particularly preferable embodiment, the agent of the present invention is in the form of a bioabsorbable gel entrapping the active ingredient peptide.

Known bioabsorbable hydrogels are suitable as the bioabsorbable gel. Specific examples include "MedGEL (trade name)", a hydrogel for sustained-release manufactured by MedGEL Corporation. This product is a water-insoluble material formed by cross-linking of gelatin and can entrap a peptide via intermolecular interaction including electrostatic interaction between the peptide and the gelatin. When the active ingredient peptide is entrapped in such a gelatin hydrogel and applied to a living body, the gelatin hydrogel is degraded by degrading enzymes such as collagenase secreted from cells. Upon hydrogel degradation, the peptide is gradually released, and the degradation product is absorbed into the living body. The shape of the bioabsorbable gel is not particularly limited, and various shapes may be employed such as a sheet, a disk, a tube, and a particle. The bioabsorbable gel can be applied or attached to a skeletal muscle injury site.

The peptide used as the active ingredient of the agent of the present invention for promoting skeletal muscle injury repair or a salt thereof is safe and less toxic, and therefore can be administered to, for example, humans and other mammals (rats, mice, rabbits, sheep, pigs, cows, cats, dogs, monkeys, etc.).

The dose may vary with the injury site, the administration route, etc. For example, in the case of intramuscular injection into the surrounding area of the skeletal muscle injury in an adult, the daily dose of the active ingredient may be about 0.00001 to 100 mg, about 0.00002 to 90 mg, about 0.00005 to 80 mg, about 0.0001 to 50 mg, about 0.01 to 30 mg, about 0.1 to 20 mg, or about 0.1 to 10 mg.

The present invention further includes the following.
(a1) A method for promoting skeletal muscle injury repair, the method comprising administering at least one peptide selected from the above-listed (1) to (4), or a salt thereof to a mammal.
(a2) A method for promoting satellite cell activation at a skeletal muscle injury site, the method comprising administering at least one peptide selected from the above-listed (1) to (4), or a salt thereof to a mammal.
(a3) A method for promoting satellite cell differentiation at a skeletal muscle injury site, the method comprising administering at least one peptide selected from the above-listed (1) to (4), or a salt thereof to a mammal.
(a4) A method for reducing scar formation at a skeletal muscle injury site, the method comprising administering at least one peptide selected from the above-listed (1) to (4), or a salt thereof to a mammal.
(b1) At least one peptide selected from the above-listed (1) to (4), or a salt thereof for use in promotion of skeletal muscle injury repair.
(b2) At least one peptide selected from the above-listed (1) to (4), or a salt thereof for use in promotion of satellite cell activation at a skeletal muscle injury site.
(b3) At least one peptide selected from the above-listed (1) to (4), or a salt thereof for use in promotion of satellite cell differentiation at a skeletal muscle injury site.
(b4) At least one peptide selected from the above-listed (1) to (4), or a salt thereof for use in reduction of scar formation at a skeletal muscle injury site.
(c1) Use of at least one peptide selected from the above-listed (1) to (4), or a salt thereof for production of an agent for promoting skeletal muscle injury repair.
(c2) Use of at least one peptide selected from the above-listed (1) to (4), or a salt thereof for production of an agent for promoting satellite cell activation at a skeletal muscle injury site.
(c3) Use of at least one peptide selected from the above-listed (1) to (4), or a salt thereof for production of an agent for promoting satellite cell differentiation at a skeletal muscle injury site.
(c4) Use of at least one peptide selected from the above-listed (1) to (4), or a salt thereof for production of an agent for reducing scar formation at a skeletal muscle injury site.

EXAMPLES

Hereinafter, the present invention will be described in detail by examples, but the present invention is not limited thereto.

Example 1: Examination of Repair Promoting Effect in Muscle Injury Model Rats (1)

1-1 Peptide Used

A peptide consisting of the amino acid sequence represented by SEQ ID NO: 1 (hereinafter referred to as "SV peptide") was used as the test peptide. The SV peptide was synthesized by the Fmoc method using a Shimadzu automated solid-phase peptide synthesizer in simultaneous multiple mode (PSSM-8; Shimadzu Corporation).

1-2 Production of Muscle Injury Model

Incisions were made in masseter muscles on both sides in Jcl:SD rats (10 weeks old). Immediately after muscle incision, 1 mL each of the SV peptide (20 ng/mL) was intramuscularly administered into several sites surrounding the cut surfaces. The incision on each side was made along a straight line connecting the lateral angle of the eye and the mandibular angle, extending in depth from the fascia on the skin side to the lateral periosteum on the mandibular ramus. The cut surfaces were subjected to electrocoagulation with an electric scalpel for the arrest of bleeding (see FIG. 1).

1-3 Behavioral Physiological Experiment (1) Experimental Method

Feeding behavior and body weight of each rat was monitored preoperatively and 1 and 2 weeks postoperatively. More specifically, each rat was housed in a transparent plastic cage of 30 cm in length×30 cm in width×30 cm in height, and the behavior was recorded on video cameras during the active time of rats (18:00 to 22:00). Food intake and mastication time were measured, and the food intake per unit of mastication time (feeding efficiency) was calculated. This experiment was performed on a muscle injury model subjected to administration of the SV peptide into the incised masseter muscles on both sides (SV group) and on a muscle injury model subjected to administration of PBS into the incised masseter muscles on both sides (PBS group).

(2) Results

Figure 2:
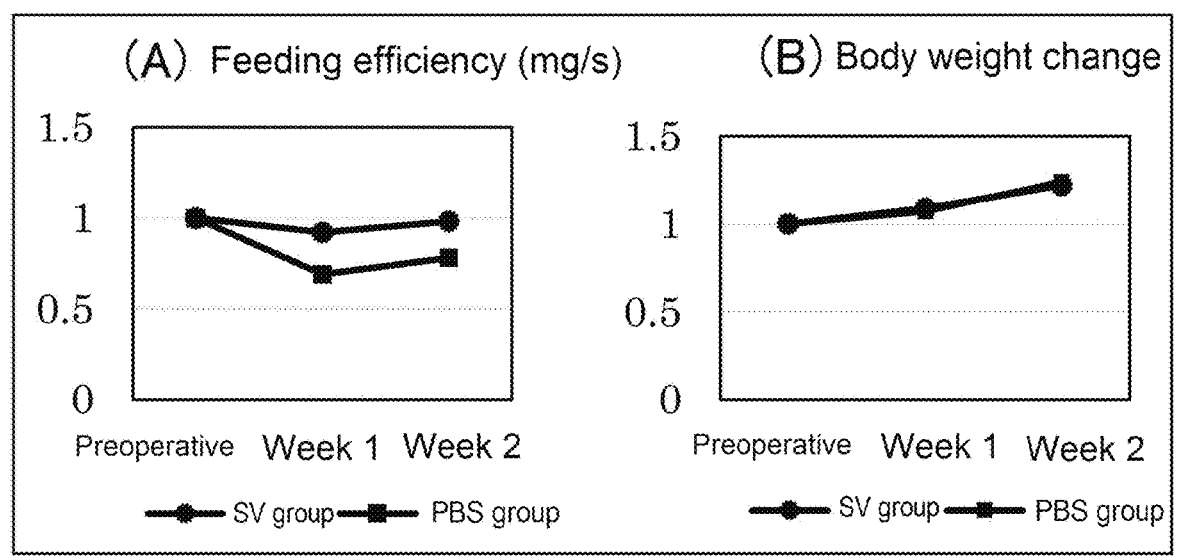
FIG. 2 shows the results of the measurement of the feeding behavior and body weight change in muscle injury model rats treated with the SV peptide (SV group) or PBS (PBS group).

The results are shown in FIG. 2. FIG. 2A is a graph showing feeding efficiency, and FIG. 2B is a graph showing body weight change. In FIGS. 2A and 2B, data were represented as relative values compared to the preoperative measured value, which was assumed as 1. The feeding efficiency in the SV group was reduced at postoperative week 1, but recovered to almost the preoperative level at postoperative week 2. On the other hand, the feeding efficiency in the PBS group was significantly reduced at postoperative week 1 and showed a tendency to recover at postoperative week 2, but the level was lower than that in the SV group. There was no difference in body weight change between the SV group and the PBS group, indicating that the food intakes in both groups were nearly equal.

1-4 Electrophysiological Experiment (1) Experimental Method

This experiment was performed on rats subjected to incision of masseter muscles on both sides and subsequent administration of the SV peptide into the incised left masseter muscle and of PBS into the incised right masseter muscle. Bipolar needle electrodes were retained in the masseter muscles on both sides, and myogenic potential signals received through connectors fixed to both sides of the parietal bone were monitored. Electromyographic (EMG) data were recorded preoperatively and 1 week postoperatively. Generally, in the electromyogram of masseter muscles recorded during food ingestion, the cutting phase and the grinding phase in the masticatory movement show different waveforms. A waveform with a smaller change in potential is presented in the cutting phase, and a waveform with a greater change in potential is presented in the grinding phase.

(2) Results

Figure 3:
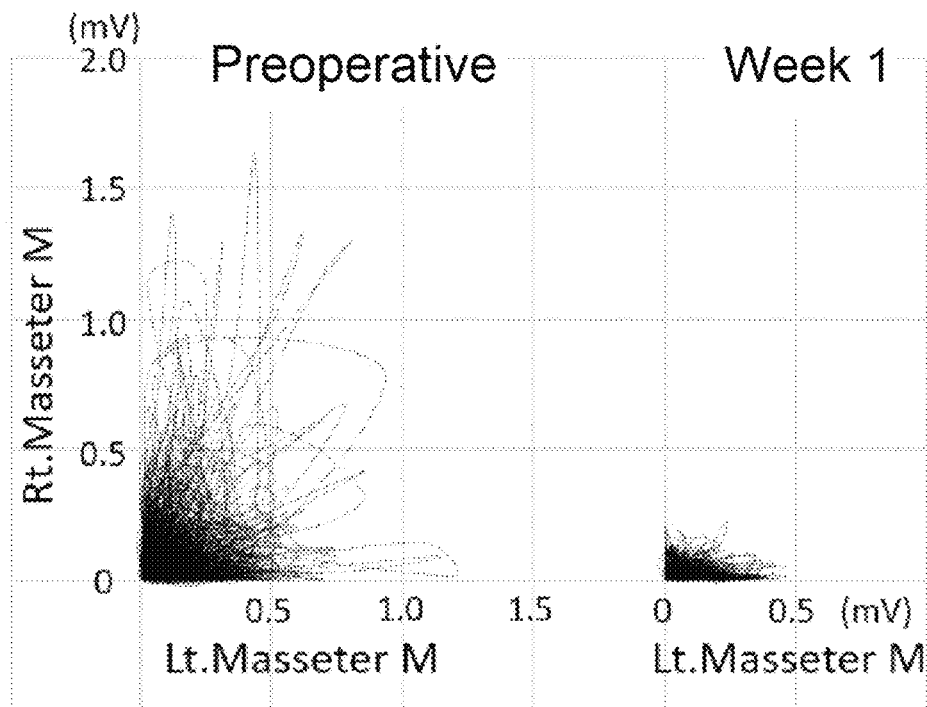
FIG. 3 shows the change in chewing side preference based on the analysis of the electromyogram of masseter muscles on both sides recorded preoperatively and 1 week postoperatively in muscle injury model rats subjected to administration of the SV peptide into the incised left masseter muscle and of PBS into the incised right masseter muscle.

From the EMG data, the myogenic potentials of the right (control side) and left (SV peptide side) masseter muscles were extracted at 0.02-second intervals and plotted on the vertical and horizontal axes, respectively, to generate a Lissajous pattern (FIG. 3). In the grinding phase, it is known that the grinding motion of the lower jaw preferentially occurs on either the right or left side. Accordingly, a high-amplitude waveform is observed on either one side in the electromyogram in an opening-and-closing motion of the mouth. A Lissajous pattern having a slope of 1 or greater was regarded as right-side chewing, and a Lissajous pattern having a slope of smaller than 1 was regarded as left-side chewing. Based on this, the chewing side preference was determined. The results show that there was a tendency to chew on the right side preoperatively while left-side chewing preference was seen postoperatively. The mean myogenic potential of the left masseter muscle during left-side chewing was reduced postoperatively, but the degree of the reduction was smaller than that in the mean myogenic potential of the right masseter muscle.

1-5 Histological Staining (1) Experimental Method

This experiment was performed on rats subjected to incision of masseter muscles on both sides and subsequent administration of the SV peptide into the incised left masseter muscle without administration into the incised right masseter muscle (control). Each rat was euthanized at postoperative week 1, and the masseter muscles on both sides were excised. Histological sections were prepared by the usual method and subjected to various types of staining. The number of immature muscle fibers with central nuclei, which were muscle fibers involved in muscle repair, and the number of blood vessels were counted on HE-staining specimens. The masseter muscle was divided into upper and lower halves in the coronal plane, and 2 slices each of the upper and lower halves were used for counting. Counting was performed in 5 fields of view in each slice. The area of granulation tissue formed on the cut surfaces was measured on sirius red-staining specimens (type I and type III collagens were stained) using an image-analysis software. The sections were immunostained for myogenin, a marker for myotube cells, and the number of myogenin-positive cells was counted using an image-analysis software.

(2) Results (2-1) Number of Blood Vessels

Figure 4:
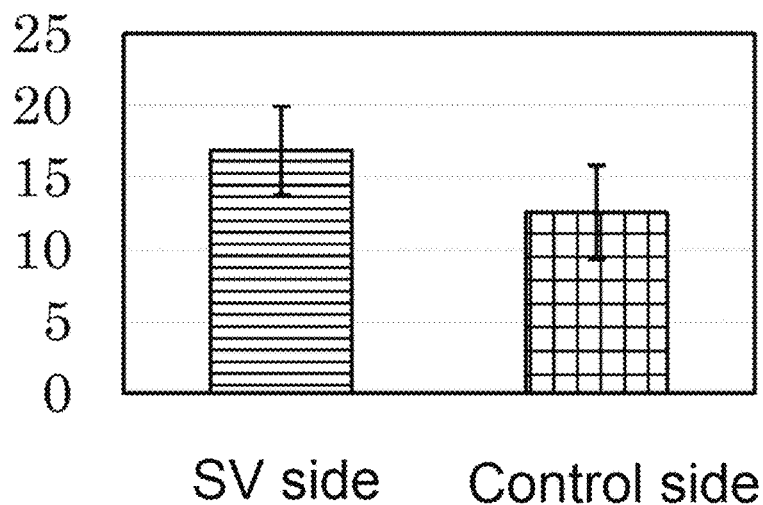
FIG. 4 shows the number of blood vessels counted on HE-staining specimens prepared by staining histological sections of masseter muscles on both sides excised at postoperative week 1 from muscle injury model rats subjected to administration of the SV peptide into the incised left masseter muscle (SV side) without administration into the incised right masseter muscle (control side).

The number of blood vessels counted per field of view is shown in FIG. 4. The number of blood vessels was significantly larger on the SV peptide side than that on the control side ($P<0.05$, t-test).

(2-2) Number of Muscle Fibers with Central Nuclei

Figure 5:
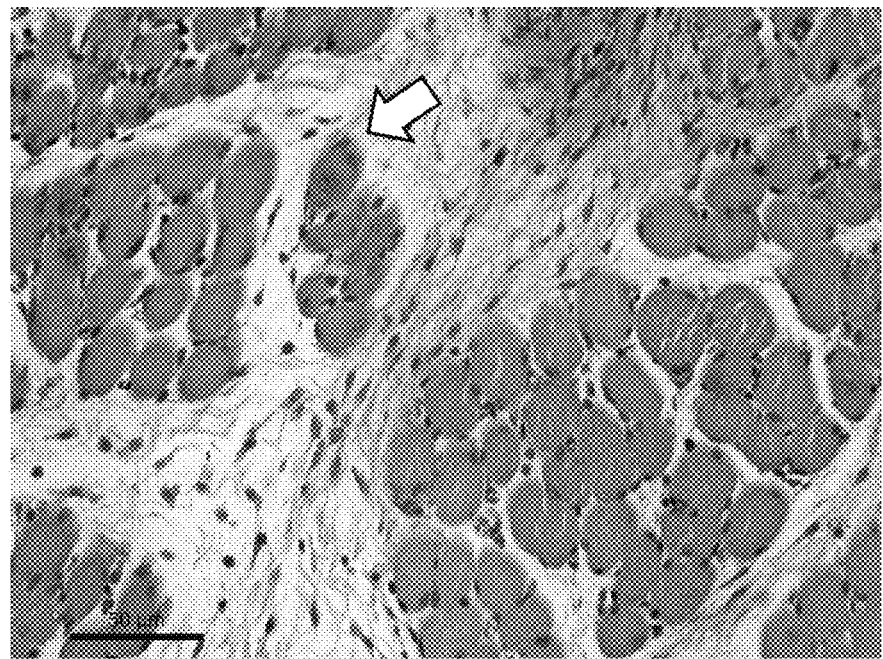
FIG. 5 show the number of muscle fibers with central nuclei counted on HE-staining specimens prepared by staining histological sections of masseter muscles on both sides excised at postoperative week 1 from muscle injury model rats subjected to administration of the SV peptide into the incised left masseter muscle without administration into the incised right masseter muscle.
Figure 5:
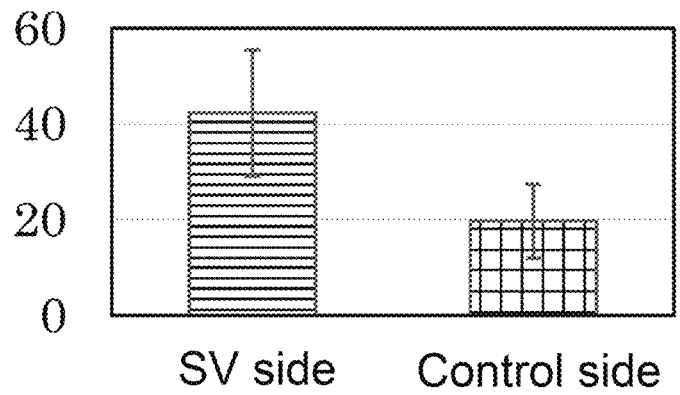

The results are shown in FIG. 5. FIG. 5A is an HE-staining image, and the arrow represents an immature muscle fiber with central nuclei. FIG. 5B is a graph showing the number of muscle fibers with central nuclei on each side. The number of muscle fibers with central nuclei was significantly larger on the SV peptide side than that on the control side ($P<0.05$, t-test).

(2-3) Area of Granulation Tissue Formed on Cut Surfaces

Figure 6:
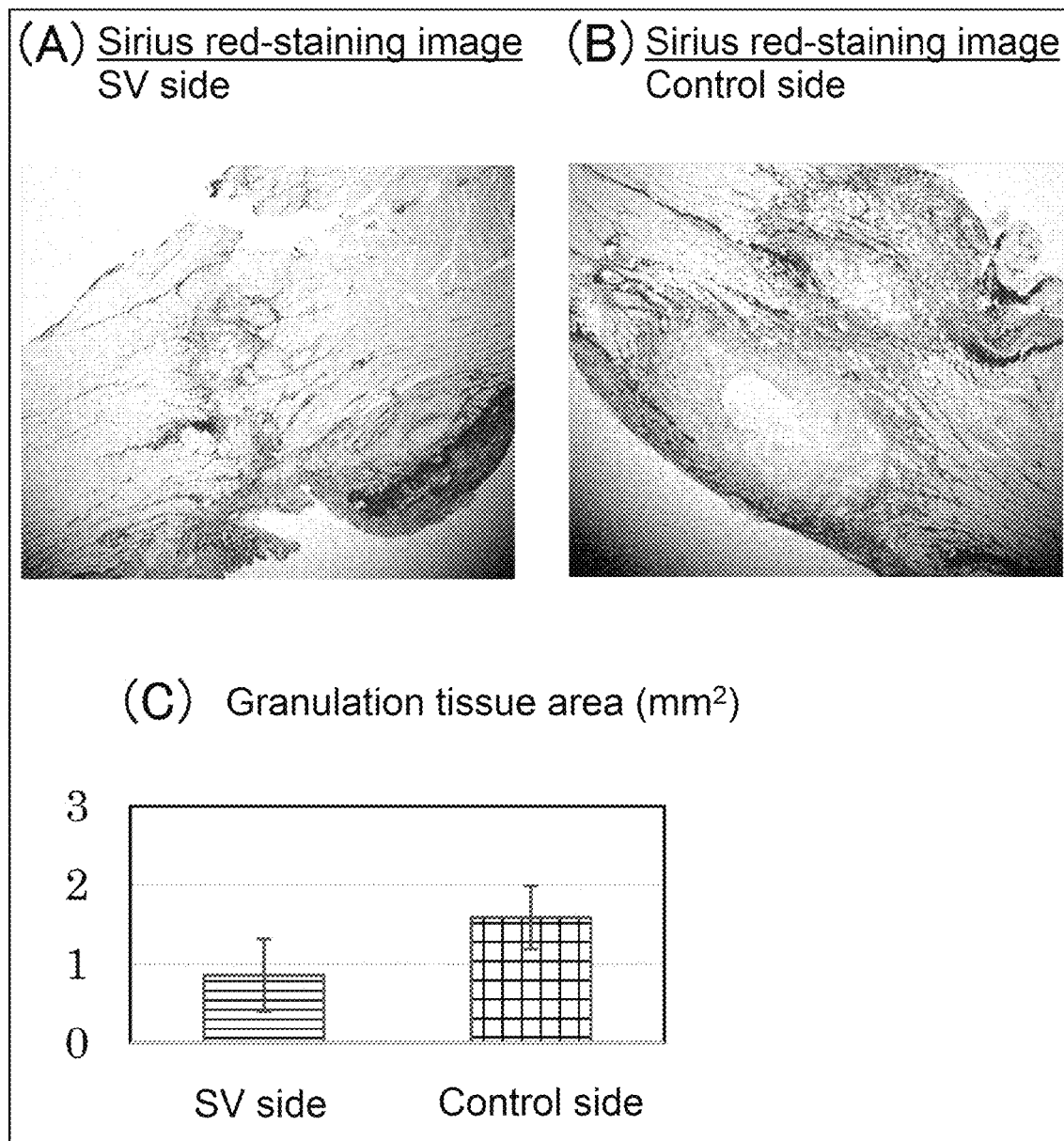
FIG. 6 shows the area of granulation tissue formed on the cut surfaces in incised masseter muscles of muscle injury model rats subjected to administration of the SV peptide into the incised left masseter muscle without administration into the incised right masseter muscle. The granulation tissue area was measured on sirius red-staining specimens prepared by staining histological sections of masseter muscles on both sides excised at postoperative week 1 from the muscle injury model rats.

The results are shown in FIG. 6. FIG. 6A is a sirius red-staining image of the SV peptide side, FIG. 6B is a sirius red-staining image of the control side, and FIG. 6C is a graph showing the granulation tissue area on each side. The granulation tissue area was significantly smaller on the SV peptide side than that on the control side ($P<0.05$, t-test).

(2-4) Number of Myogenin-Positive Nuclei

Figure 7:
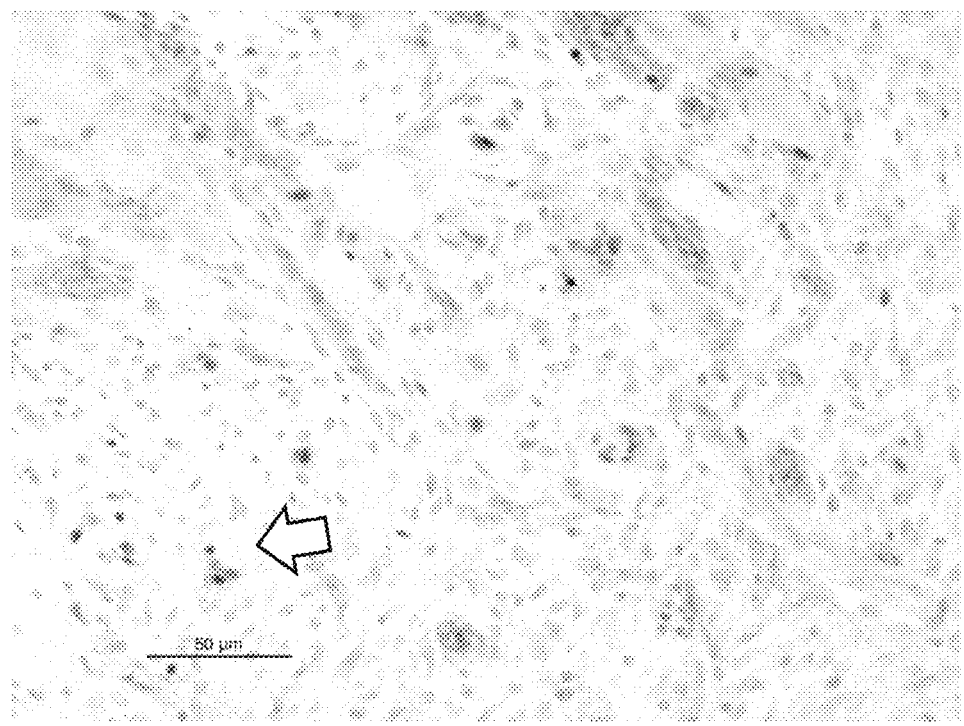
FIG. 7 shows the number of myogenin-positive nuclei counted on myogenin-immunostained specimens prepared by staining histological sections of masseter muscles on both sides excised at postoperative week 1 from muscle injury model rats subjected to administration of the SV peptide into the incised left masseter muscle without administration into the incised right masseter muscle.
Figure 7:
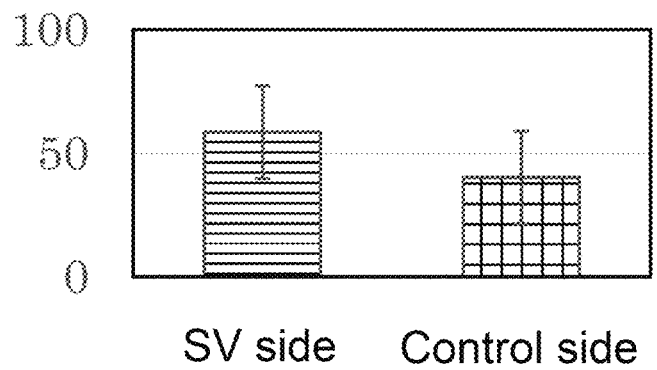

The results are shown in FIG. 7. FIG. 7A is an immunostaining image for myogenin, and the arrow represents a muscle fiber (myotube cell) with dark-stained nuclei. FIG. 7B is a graph showing the number of myogenin-positive nuclei per field of view on each side. The number of myogenin-positive nuclei was significantly larger on the SV peptide side than that on the control side ($P<0.05$, t-test).

The above results show that the SV peptide administered in the surrounding area of a skeletal muscle injury site remarkably promotes repair at the injury site. Such repair promotion can result from SV peptide-promoted satellite cell activation and differentiation.

Example 2: Examination of Repair Promoting Effect in Muscle Injury Model Rats (2)

2-1 Peptide Used

The SV peptide synthesized using the same synthesizer as used in Example 1 was used.

2-2 Production of Muscle Injury Model

Incisions were made in masseter muscles on both sides in Jcl:SD rats (10 weeks old) under anesthesia in the same manner as in Example 1. Immediately after muscle incision, 1 mL each of the SV peptide (20 ng/mL) or 1 mL each of PBS was intramuscularly administered into several sites surrounding the cut surfaces. The incision on each side was made along a straight line connecting the lateral angle of the eye and the mandibular angle, extending in depth from the fascia on the skin side to the lateral periosteum on the mandibular ramus. The cut surfaces were subjected to electrocoagulation with an electric scalpel for the arrest of bleeding (see FIG. 1). In Example 2, the experiment was performed on rats subjected to incision of masseter muscles on both sides and subsequent administration of the SV peptide into the incised left masseter muscle without administration into the incised right masseter muscle (SV group) and on rats subjected to incision of masseter muscles on both sides and subsequent administration of PBS into the incised left masseter muscle without administration into the incised right masseter muscle (PBS group).

2-3 Behavioral Physiological Experiment (1) Experimental Method

In the same manner as in Example 1, each rat was housed in a transparent plastic cage of 30 cm in length×30 cm in width×30 cm in height at postoperative weeks 1, 2, 4, 6, and 8, and the behavior was recorded on video cameras during the active time of rats (18:00 to 22:00). Food intake and mastication time were measured, and the food intake per unit of mastication time (feeding efficiency) was calculated.

(2) Results

Figure 8:
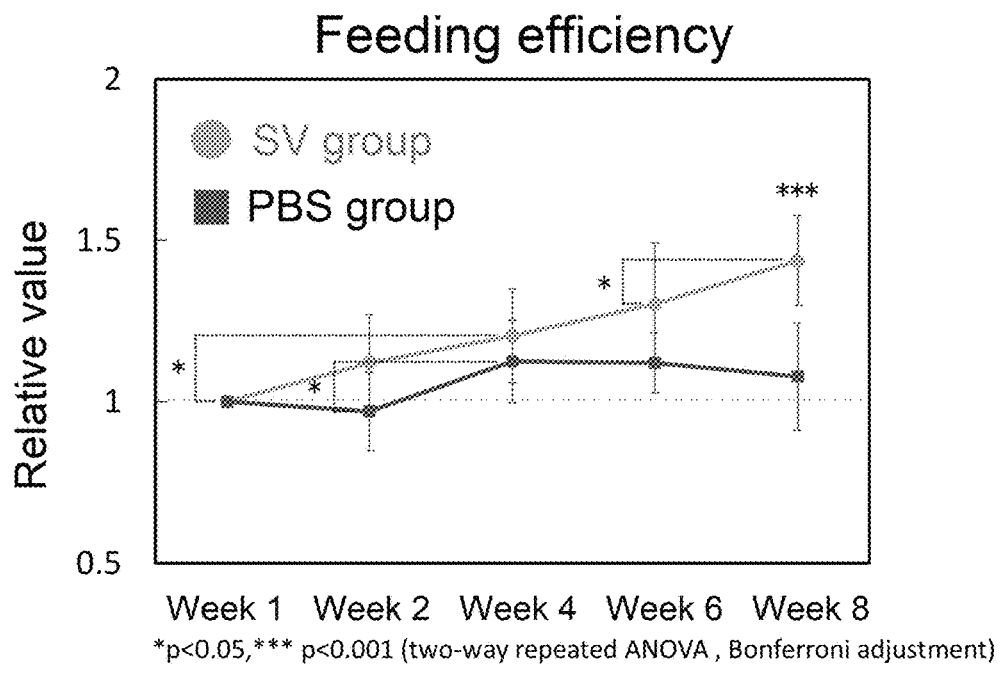
FIG. 8 shows the feeding efficiency (the food intake per unit of mastication time) at postoperative weeks 1, 2, 4, 6, and 8 in rats subjected to incision of masseter muscles on both sides and subsequent administration of the SV peptide into the incised left masseter muscle without administration into the incised right masseter muscle (SV group) and in rats subjected to incision of masseter muscles on both sides and subsequent administration of PBS into the incised left masseter muscle without administration into the incised right masseter muscle (PBS group).

The results are shown in FIG. 8. Feeding efficiency was represented as a relative value compared to the 1-week postoperative measured value, which was assumed as 1. The PBS group did not show a great improvement in feeding efficiency at postoperative week 4 and thereafter, while the SV group showed a time-dependent improvement in feeding efficiency. The SV group showed a significantly higher value than that in the PBS group at postoperative week 8.

2-4 Electrophysiological Experiment (1) Experimental Method

In the same manner as in Example 1, bipolar needle electrodes were retained in the masseter muscles on both sides, and myogenic potential signals received through connectors fixed to both sides of the parietal bone were monitored. EMG data were recorded at postoperative weeks 1, 2, 4, 6, and 8.

(2) Results

Figure 9:
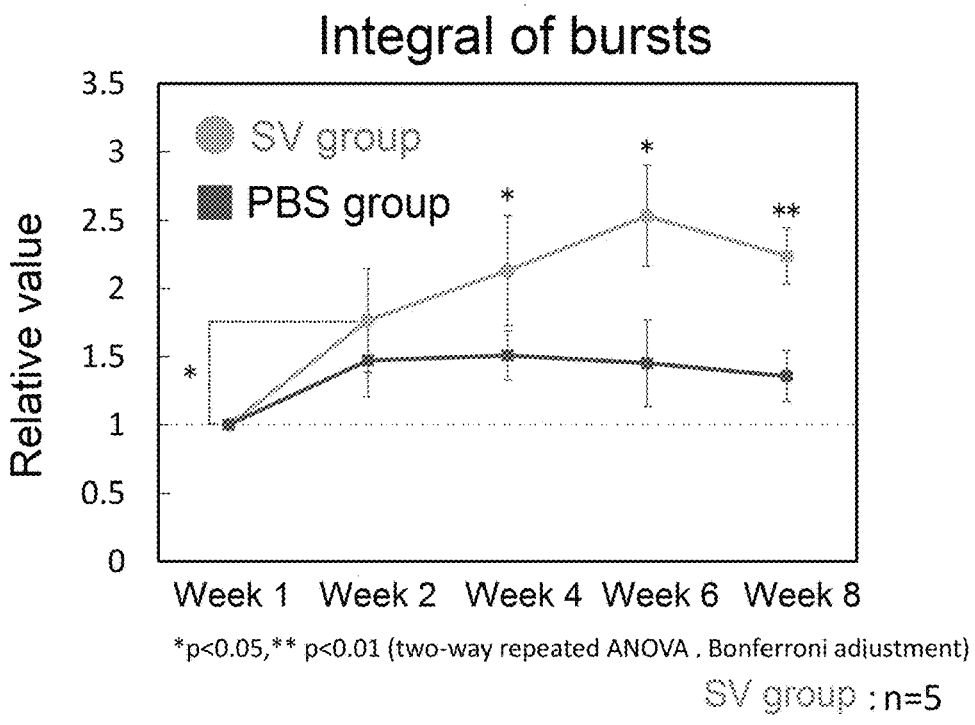
FIG. 9 shows the time course change of the integral of bursts in the electromyogram of the left masseter muscle recorded at postoperative weeks 1, 2, 4, 6, and 8 in rats subjected to incision of masseter muscles on both sides and subsequent administration of the SV peptide into the incised left masseter muscle without administration into the incised right masseter muscle (SV group) and in rats subjected to incision of masseter muscles on both sides and subsequent administration of PBS into the incised left masseter muscle without administration into the incised right masseter muscle (PBS group).

The integral of bursts in the left (administration side) masseter muscle in the SV group or the PBS group was calculated as a measure of muscle activity and represented in FIG. 9 as a relative value compared to the 1-week postoperative value, which was assumed as 1. The SV group showed significantly greater values than those in the PBS group at weeks 4, 6, and 8.

Figure 10:
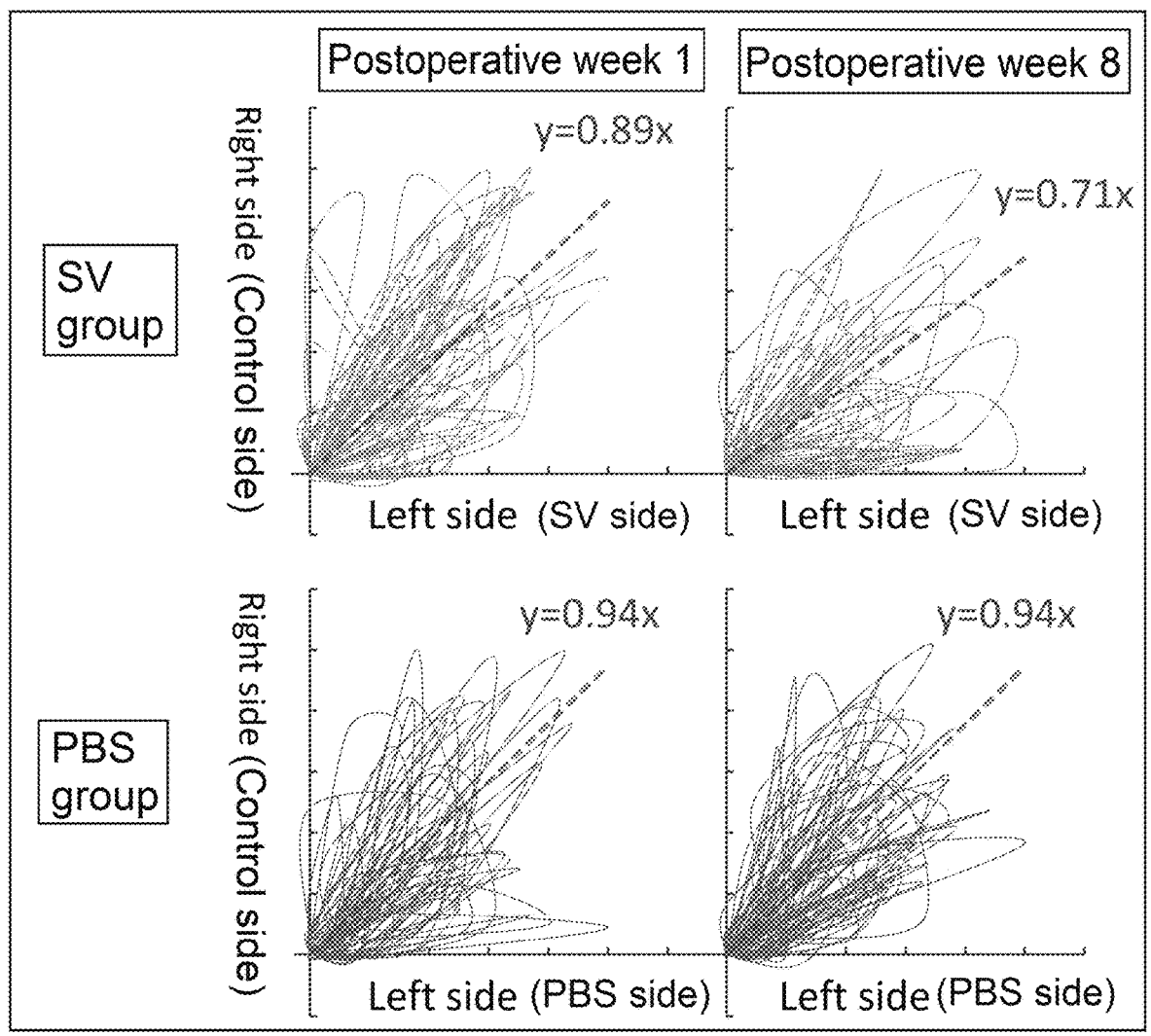
FIG. 10 shows the change in chewing side preference based on the analysis of the electromyogram of masseter muscles on both sides recorded at postoperative weeks 1 and 8 in rats subjected to incision of masseter muscles on both sides and subsequent administration of the SV peptide into the incised left masseter muscle without administration into the incised right masseter muscle (SV group) and in rats subjected to incision of masseter muscles on both sides and subsequent administration of PBS into the incised left masseter muscle without administration into the incised right masseter muscle (PBS group).

From the EMG data, the myogenic potentials of the right (control side: incision only) and left (SV peptide side or PBS side) masseter muscles were extracted at 0.02-second intervals and plotted on the vertical and horizontal axes, respectively, to generate a Lissajous pattern (FIG. 10). A Lissajous pattern having a slope of 1 or greater was regarded as right-side chewing, and a Lissajous pattern having a slope of smaller than 1 was regarded as left-side chewing. Based on this, the chewing side preference was determined. The SV group showed an increase in left-side chewing preference over time postoperatively, but such a tendency was not observed in the PBS group.

2-5 CT Image Analysis (1) Experimental Method

Images were taken at postoperative week 8 using a micro CT for laboratory animals (Rigaku, tube voltage: 90 kV, tube current: 160 µA, voxel size: 118 µm). From the obtained DICOM data, MPR images were created in parallel to a plane passing through the tip of the anterior nasal spine and the superior borders of both mandibular heads. On the image at the level of the occlusal plane including the masseter muscle incision site, the muscle cross-sectional area (CSA), the mean CT value, and the % CSA (the percentage of the area having a muscle CT value in the area of interest) were measured and compared.

(2) Results

Figure 11:
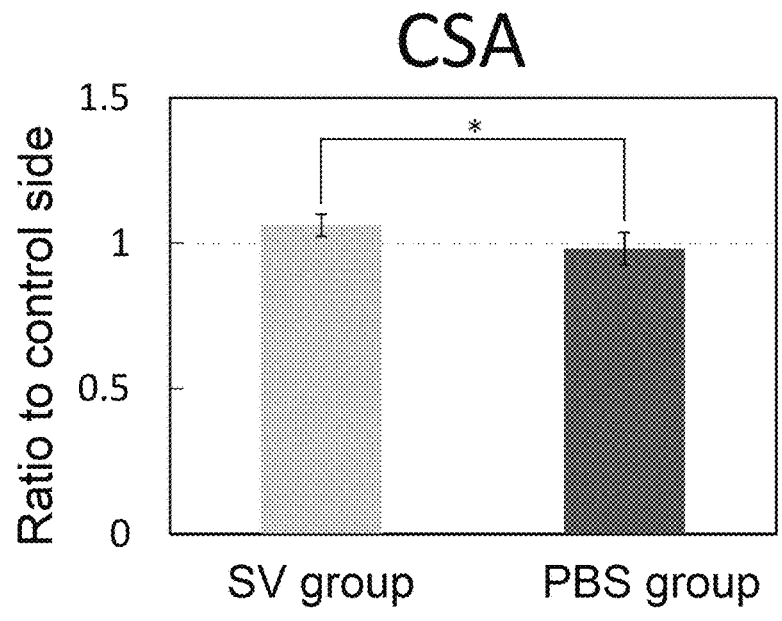
FIG. 11 shows the muscle cross-sectional area (CSA) on the CT image at the level of the occlusal plane including the masseter muscle incision site at postoperative week 8 in rats subjected to incision of masseter muscles on both sides and subsequent administration of the SV peptide into the incised left masseter muscle without administration into the incised right masseter muscle (SV group) and in rats subjected to incision of masseter muscles on both sides and subsequent administration of PBS into the incised left masseter muscle without administration into the incised right masseter muscle (PBS group).

The results of CSA are shown in FIG. 11. The SV group showed a significantly greater CSA in the area including the muscle incision site than that in the corresponding area in the PBS group.

Figure 12:
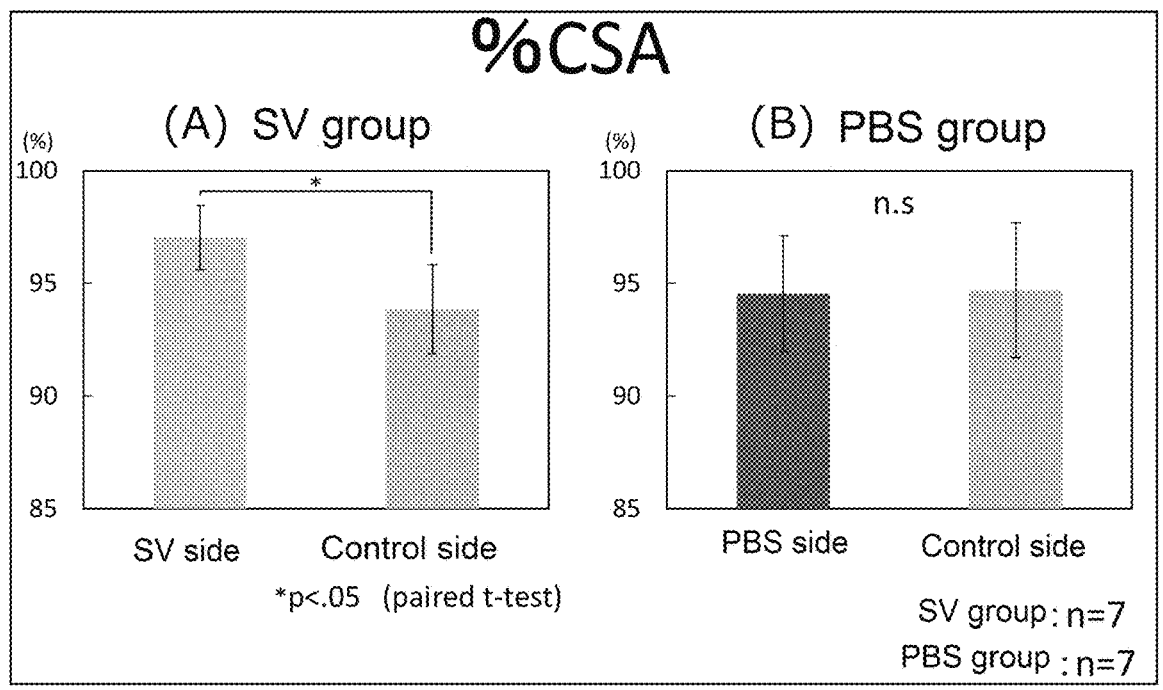
FIG. 12 shows the % CSA (the percentage of the area having a muscle CT value in the area of interest) on the CT image at the level of the occlusal plane including the masseter muscle incision site at postoperative week 8 in rats subjected to incision of masseter muscles on both sides and subsequent administration of the SV peptide into the incised left masseter muscle without administration into the incised right masseter muscle (SV group) and in rats subjected to incision of masseter muscles on both sides and subsequent administration of PBS into the incised left masseter muscle without administration into the incised right masseter muscle (PBS group).

The results of % CSA are shown in FIG. 12. FIG. 12A shows the results for the SV group, and FIG. 12B shows the results for the PBS group. The SV group showed a significantly higher % CSA on the left side with SV administration (SV side) than that on the right side without administration (control side). In contrast, in the PBS group, there was no difference between the left side (PBS side) and the right side (control side).

2-6 Histological Staining (1) Experimental Method

Each rat was euthanized at postoperative week 8, and the masseter muscles on both sides were excised. The masseter muscles were embedded in paraffin and transversally sliced into histological sections by the usual method. The sections were subjected to HE staining and sirius red staining. Histological characteristics of regenerated muscle fibers at the muscle injury site were assessed on the HE-stained sections. The amount of muscle fibers formed and the diameter of the muscle fibers in the tissue were measured on the sirius red-staining sections.

These data were compared between the groups.

(2) Results

Observation of the HE-staining specimens confirmed the formation of mature muscle fibers having a striated pattern even at the muscle injury site without administration of the SV peptide.

Figure 13:
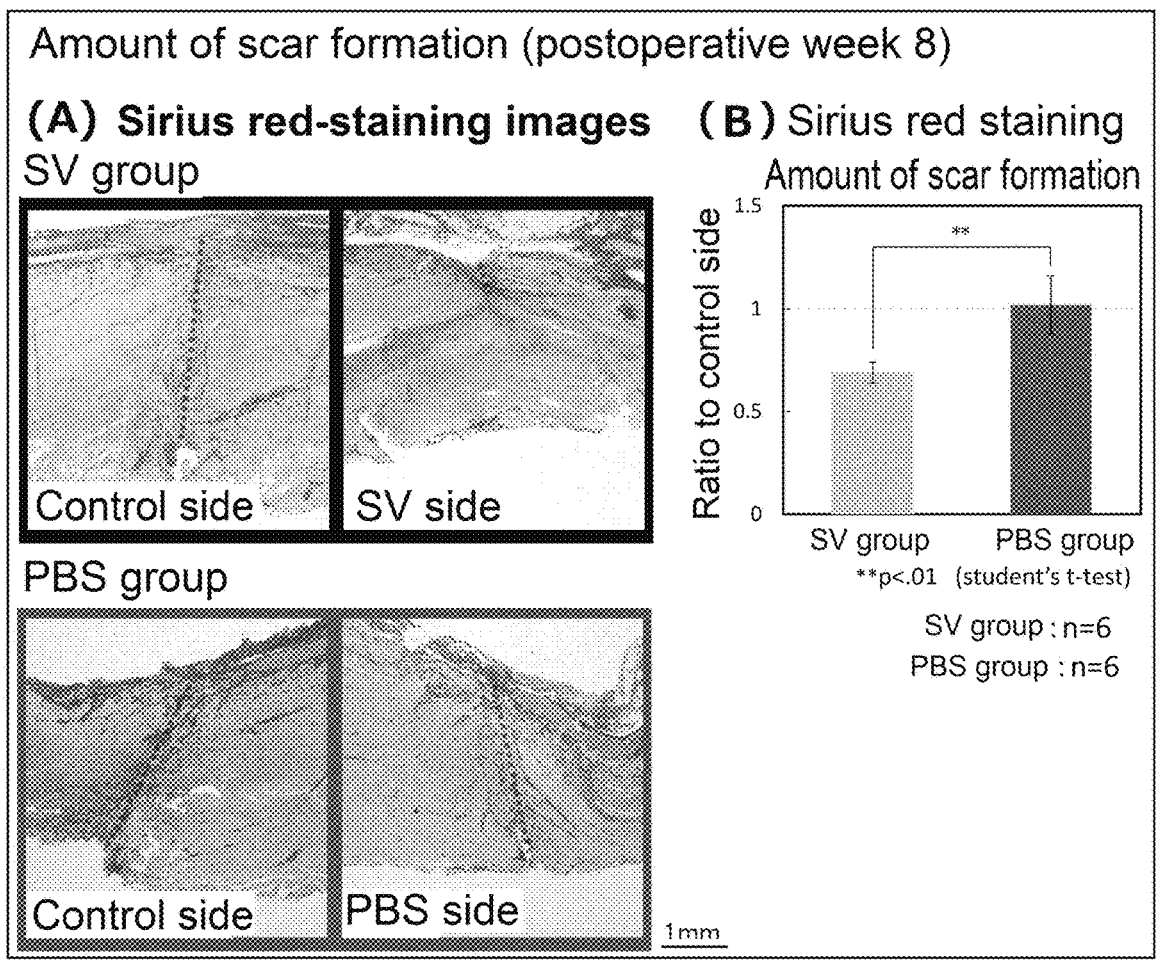
FIG. 13 shows the results of the evaluation of the amount of scar formation at the muscle injury site in rats subjected to incision of masseter muscles on both sides and subsequent administration of the SV peptide into the incised left masseter muscle without administration into the incised right masseter muscle (SV group) and in rats subjected to incision of masseter muscles on both sides and subsequent administration of PBS into the incised left masseter muscle without administration into the incised right masseter muscle (PBS group). The amount of scar formation was measured on sirius red-staining specimens prepared by staining histological sections of masseter muscles on both sides excised at postoperative week 8 from the rats in both groups.

The results of the evaluation of the amount of scar formation at the muscle injury site are shown in FIG. 13. FIG. 13A presents sirius red-staining images in the SV group and in the PBS group. FIG. 13B shows the results of the measurement of the area of scar tissue formed on the cut surfaces (dashed line in the figure) using an image-analysis software. The amount of scar formation on the SV peptide administration side in the SV group was remarkably reduced from that on the PBS administration side in the PBS group.

Figure 14:
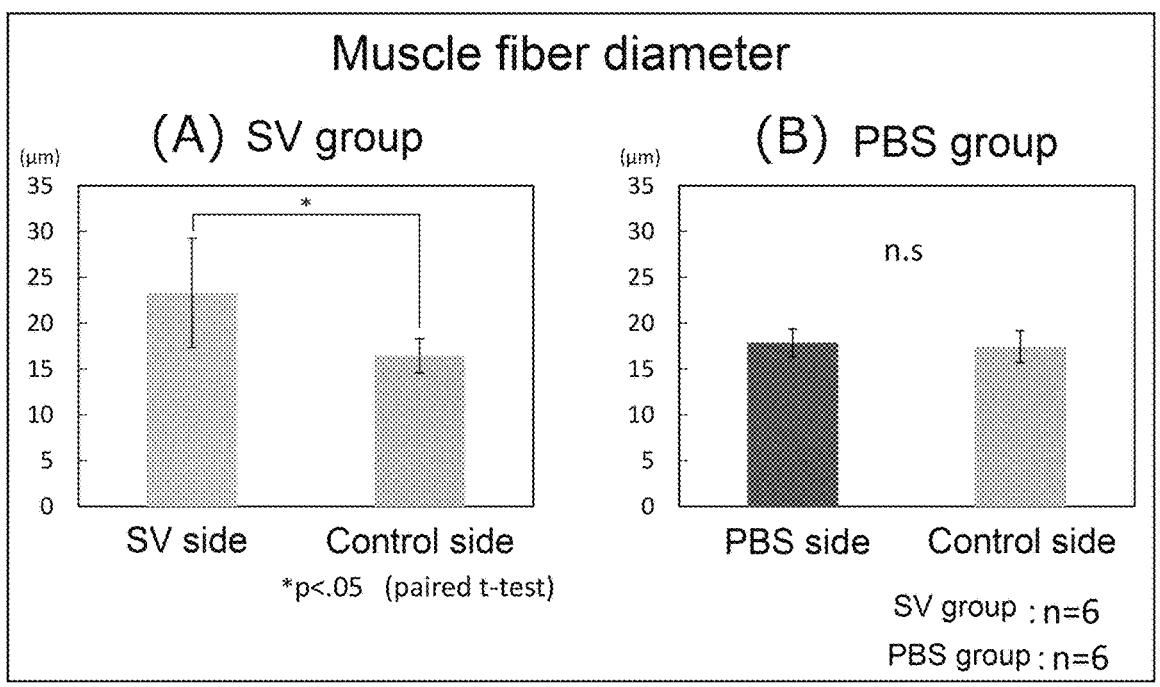
FIG. 14 shows the diameter of muscle fibers measured on sirius red-staining specimens prepared by staining histological sections of masseter muscles on both sides excised at postoperative week 8 from rats subjected to incision of masseter muscles on both sides and subsequent administration of the SV peptide into the incised left masseter muscle without administration into the incised right masseter muscle (SV group) and from rats subjected to incision of masseter muscles on both sides and subsequent administration of PBS into the incised left masseter muscle without administration into the incised right masseter muscle (PBS group).
Figure 15:
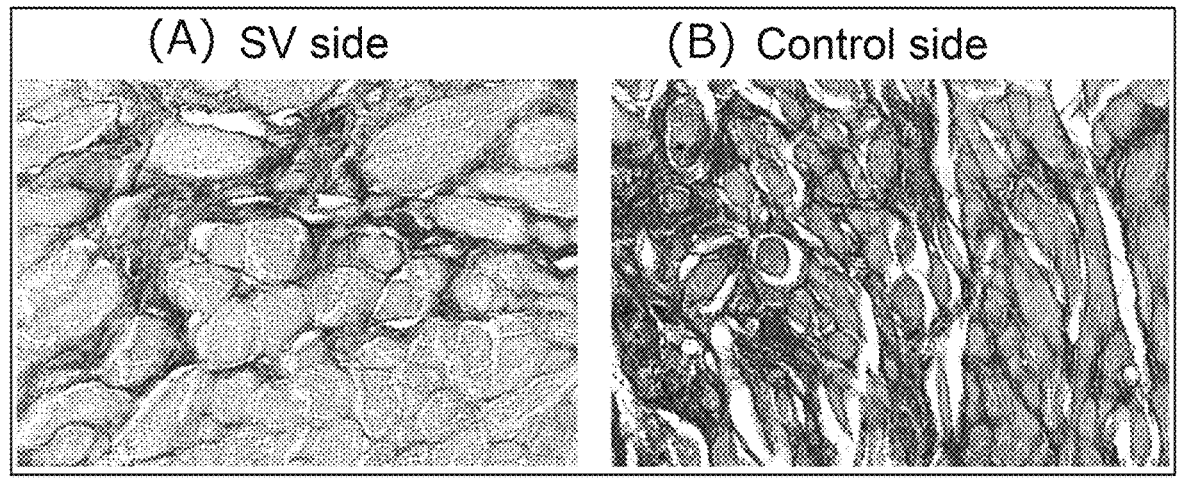
FIG. 15 presents images of sirius-red staining specimens for measuring the diameter of muscle fibers in rats subjected to incision of masseter muscles on both sides and subsequent administration of the SV peptide into the incised left masseter muscle without administration into the incised right masseter muscle (SV group).

FIG. 14 shows the results of the measurement of the diameter of the muscle fibers. FIG. 15 presents highly magnified sirius red-staining images in the SV group. FIG. 15A is an image of the SV peptide administration side (SV side), and FIG. 15B is an image of the non-administration side (control side). As is clear from FIGS. 14 and 15, the diameter of the muscle fibers on the SV side in the SV group was significantly larger than that on the control side in the same group, showing that mature muscle fibers were formed.

The above results show that the tear injury inflicted on rat masseter muscles spontaneously recovered to some extent through tissue regeneration and repair, but administration of the SV peptide remarkably promoted repair at the injury site, resulting in a greater increase in feeding efficiency. In addition, it became evident morphologically and histologically that administration of the SV peptide reduces scar formation at an injury site and induces regeneration and repair associated with mature muscle fibers.

Example 3: In Vitro Cell Biological Examination of SV peptide 3-1 Peptide Used

The SV peptide and a loss-of-function SV peptide in which the amino acids composing the SV peptide were randomly arranged to disrupt the function of the SV peptide (hereinafter called "random SV") were synthesized using the same synthesizer as used in Example 1 and used. The amino acid sequence of the random SV was GYRVLSV (SEQ ID NO: 6).

3-2 Cells

Human skeletal muscle satellite cells (HskMSCs) were purchased from ScienCell Research Laboratories and used. The medium used for HskMSC culture was the supplier's recommended medium (Skeletal Muscle Cell Medium containing 5% FBS, Skeletal Muscle Cell Growth Supplement, and penicillin/streptomycin solution).

Human skeletal muscle myoblasts (HSMMs) were purchased from Lonza and used. The medium used for HSMM culture was the supplier's recommended medium (Skeletal Muscle Growth Media-2 supplemented with SingleQuots Kit).

3-3 Examination of Cell Proliferative Capacity (1) Experimental Method

Human skeletal muscle satellite cells and human skeletal muscle myoblasts were separately seeded at $1.0 \times 10^4$ cells/mL in each well of non-treated polystyrene 96-well cell culture plates (Falcon). The SV peptide (20 ng/mL, SV group), the random SV (20 ng/mL, random SV group), or PBS (PBS group) was added to the medium. The plates were cultured at 37° C. in a 5% $CO_2$ atmosphere. After 0, 12, 24, 48, and 72 hours, cell proliferation was assessed using Premix WST-1 Cell Proliferation Assay System (Takara Bio, Japan).

(2) Results

Figure 16:
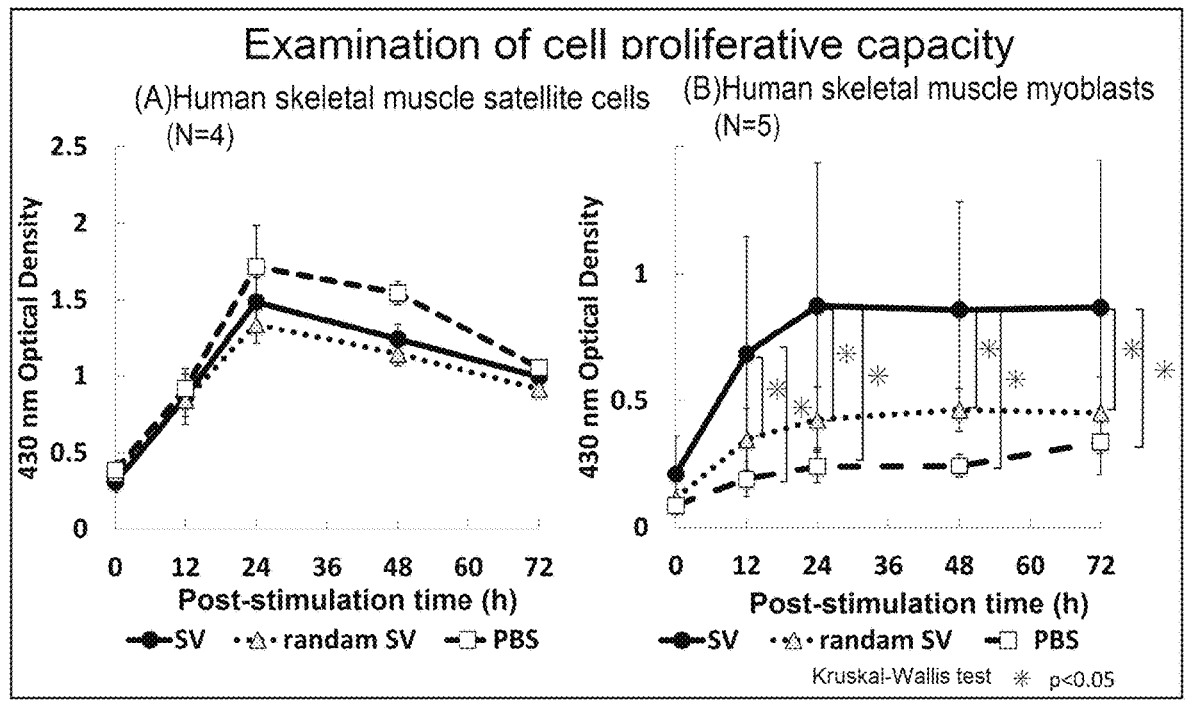
FIG. 16 shows the results of the examination of the effect of the SV peptide on the cell proliferative capacity of human skeletal muscle satellite cells and human skeletal muscle myoblasts.

The results are shown in FIG. 16. FIG. 16A shows the results for human skeletal muscle satellite cells, and FIG. 16B shows the results for human skeletal muscle myoblasts. The cell proliferative capacity of human skeletal muscle satellite cells was not enhanced by the SV peptide. The cell proliferative capacity of human skeletal muscle myoblasts was significantly increased after 24-hour treatment with the SV peptide and then reached a plateau. The cell proliferative capacity in the SV group was significantly higher at 12 hours post-treatment and remained significantly higher thereafter than that in the PBS group or the random SV group.

3-4 Examination of Chemotactic Capacity (1) Experimental Method

A polycarbonate membrane with a pore size of 8 µm (Chemotaxicell: Kurabo Industries LTD.) was immersed in a 10 µg/mL fibronectin solution at room temperature for 30 minutes for coating the membrane. A medium containing the SV peptide (20 ng/mL, SV group), the random SV (20 ng/mL, random SV group), or PBS (PBS group) as a chemoattractant was added to a lower chamber. On an upper chamber, human skeletal muscle satellite cells and human skeletal muscle myoblasts were separately seeded at $2.0 \times 10^4$ cells/mL in DMEM containing 0.1% BSA. A pair of chambers was incubated at 37° C. for 12 hours. The cells on the upper surface of the membrane were removed with a swab, and the membrane was fixed with a 10% neutral buffered formalin solution (Wako Pure Chemical Industries, Ltd.) and stained with hematoxylin. The number of cells migrated to the lower surface of the membrane was measured under an optical microscope.

(2) Results

Figure 17:
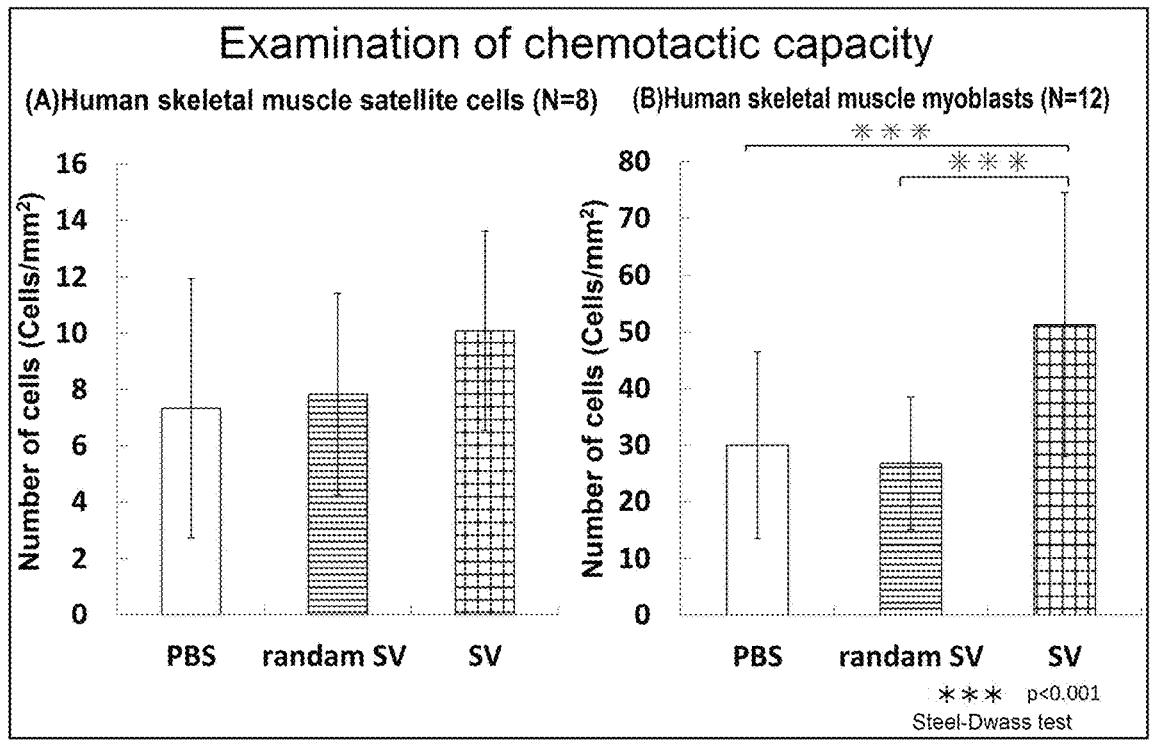
FIG. 17 shows the results of the examination of the effect of the SV peptide on the chemotactic capacity of human skeletal muscle satellite cells and human skeletal muscle myoblasts.

The results are shown in FIG. 17. FIG. 17A shows the results for human skeletal muscle satellite cells, and FIG. 17B shows the results for human skeletal muscle myoblasts. The human skeletal muscle satellite cells in the SV group tended to have a higher chemotactic capacity than that of the counterpart in the PBS group or the random SV group, but there was no significant intergroup difference. The human skeletal muscle myoblasts in the SV group had a significantly higher chemotactic capacity than that of the counterpart in the PBS group or the random SV group.

3-5 Examination of Cell Migratory Capacity (1) Experimental Method

Human skeletal muscle satellite cells and human skeletal muscle myoblasts were separately cultured on 60-mm (diameter) dishes (Iwaki) to 100% confluency. From each dish, a 2-mm-wide strip of cells were removed, and the medium was replaced with a medium containing the SV peptide (20 ng/mL, SV group), the random SV (20 ng/mL, random SV group), or PBS (PBS group). Thereafter, culture was continued. Images were taken with a digital camera mounted on a phase-contrast microscope every 12 hours. The cell-denuded area was measured using the image-analysis software ImageJ (NIH, USA). The cell migration percentage was determined by calculating the percentage of reduction in the cell-denuded area relative to the value immediately after cell removal.

(2) Results

Figure 18:
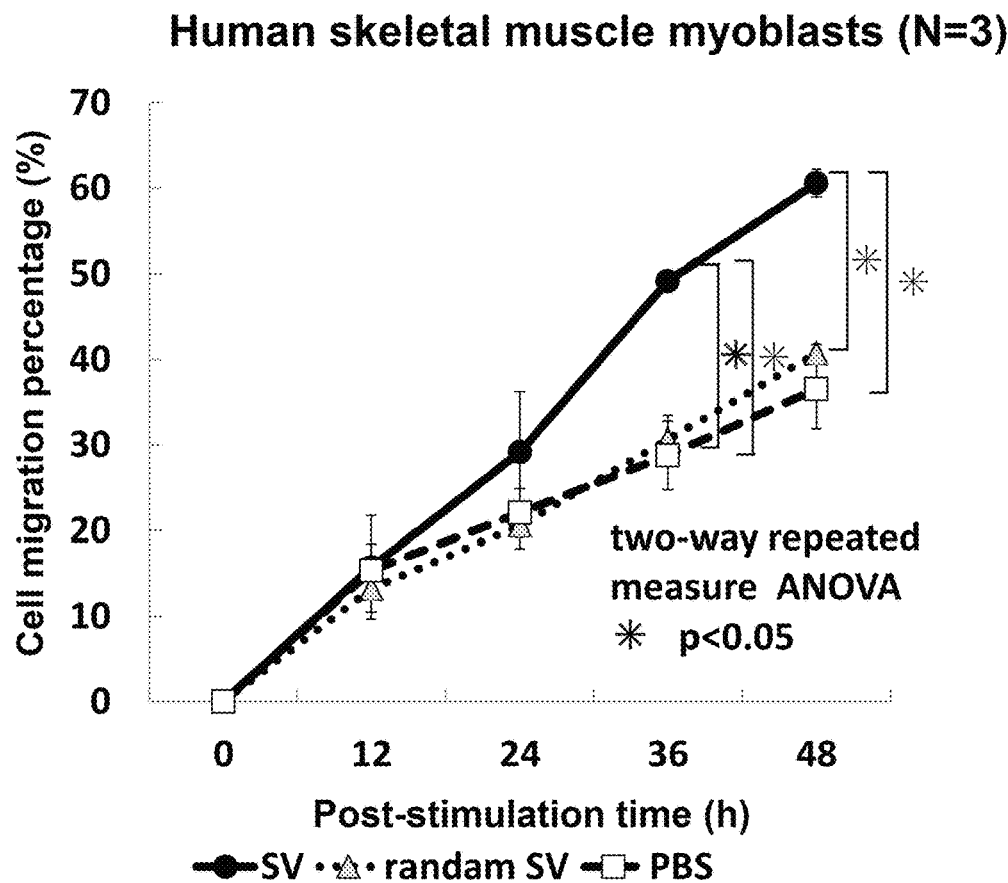
FIG. 18 shows the results of the examination of the effect of the SV peptide on the cell migratory capacity of human skeletal muscle myoblasts.

The results for human skeletal muscle myoblasts are shown in FIG. 18. The cell migratory capacity in the SV group was higher than that in the PBS group or the random SV group at 24 hours after cell removal and thereafter, and was significantly different from that in the PBS group or the random SV group at 36 and 48 hours after cell removal. The SV peptide did not affect the cell migratory capacity of human skeletal muscle satellite cells.

3-6 Confirmation of Myogenin Expression by Immunofluorescence Staining

Myogenin is known to be expressed when myoblasts differentiate into myotube cells. In this experiment, myogenin expression was used as an index to examine the effect of the SV peptide on the differentiation of human skeletal muscle myoblasts.

(1) Experimental Method

Human skeletal muscle myoblasts were cultured in a medium containing the SV peptide (20 ng/mL, SV group), the random SV (20 ng/mL, random SV group), or PBS (PBS group) for 48 or 72 hours. For a positive control, human skeletal muscle myoblasts were cultured in an F-12/DMEM medium containing 2% horse serum, which is known to facilitate myoblast differentiation into myotube cells (Moira A. Lawson et al.: Cells Tissues Organs 2000; 167: 130-137) (HS group). After 48- or 72-hour culture, the cells were immunostained with an anti-human myogenin antibody by the usual method and observed with a fluorescence microscope.

(2) Results

Figure 19:
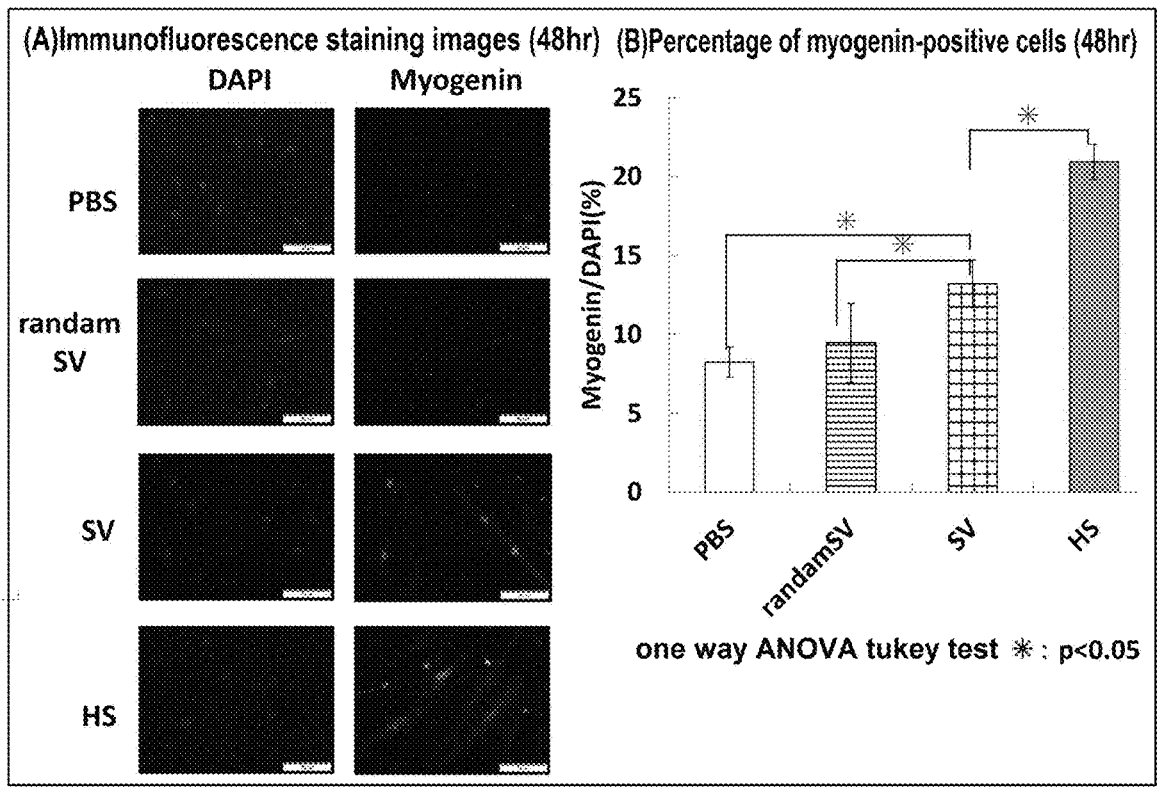
FIG. 19 shows the results of immunofluorescence staining for detection of myogenin expression and the percentage of myogenin-positive cells after 48-hour culture of human skeletal muscle myoblasts in a medium containing the SV peptide or a control substance.
Figure 20:
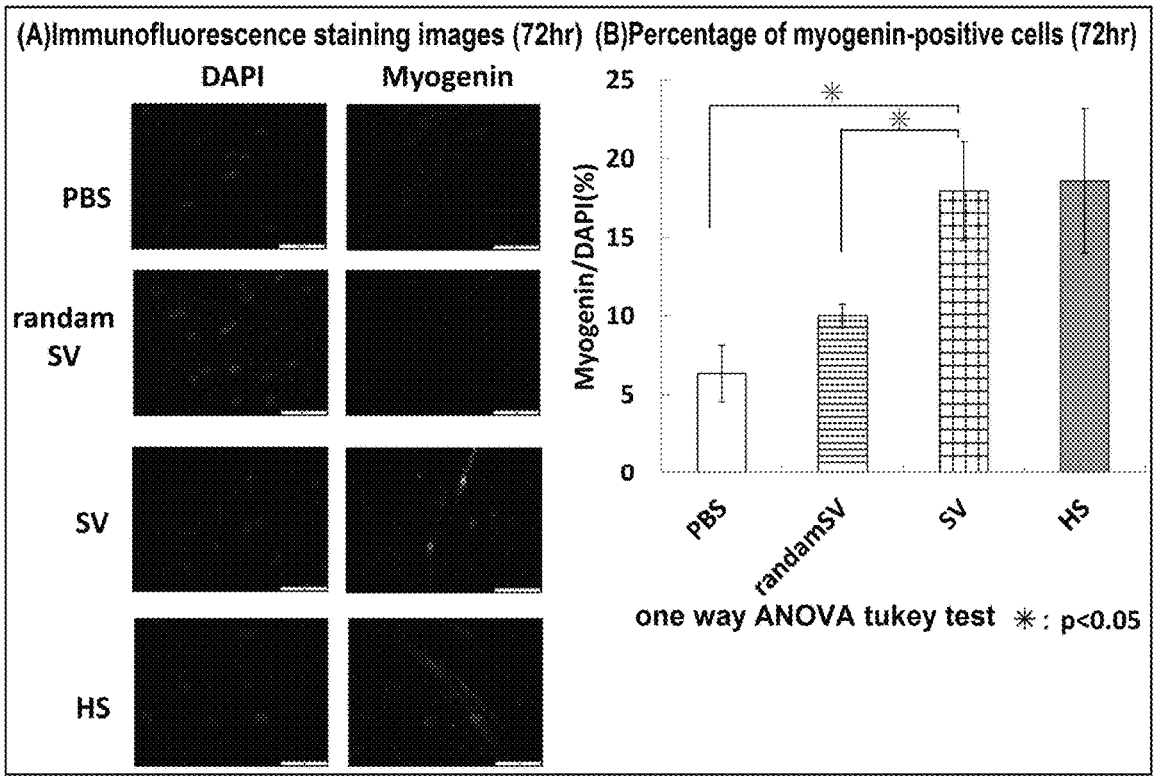
FIG. 20 shows the results of immunofluorescence staining for detection of myogenin expression and the percentage of myogenin-positive cells after 72-hour culture of human skeletal muscle myoblasts in a medium containing the SV peptide or a control substance.

The results of 48-hour culture are shown in FIG. 19, and the results of 72-hour culture are shown in FIG. 20. FIGS. 19A and 20A present fluorescence microscopic images, and FIGS. 19B and 20B are graphs showing the percentages of myogenin-positive cells. In FIGS. 19A and 20A, the left panels are DAPI-staining (nuclear staining) images, and the right panels are myogenin-immunostained images. As is shown by the results of 48-hour culture (FIG. 19), the percentage of myogenin-positive cells in the SV group was significantly higher than that in the PBS group or the random SV group, but significantly lower than that in the HS group. As is shown by the results of 72-hour culture (FIG. 20), the percentage of myogenin-positive cells in the SV group was significantly higher than that in the PBS group or the random SV group, and comparable to that in the HS group.

The above results show that the SV peptide remarkably enhances cell proliferative capacity, chemotactic capacity, and cell migratory capacity of human skeletal muscle myoblasts. The SV peptide does not directly act on human skeletal muscle satellite cells, but is likely to enhance the functions of myoblasts, which are differentiated cells from the satellite cells, resulting in promotion of regeneration and repair of injured muscle tissue. In addition, the increase in myogenin expression level in human skeletal muscle myoblasts as shown above indicates that the SV peptide is involved in promoting myoblast differentiation into myotube cells.

Example 4: Examination of In Vivo Skeletal Muscle Forming Capability (1) Experimental Method In the same manner as in Example 2, incisions were made in masseter muscles on both sides in Jcl:SD rats (10 weeks old) under anesthesia, and immediately after that, the rats were subjected to administration of 1 mL of the SV peptide (20 ng/mL) or 1 mL of PBS into the incised left masseter muscle without administration into the incised right masseter muscle. The two groups were called "SV group" and "PBS group". Each rat was euthanized at postoperative week 1, and the masseter muscles on both sides were excised. The masseter muscles were embedded in paraffin and transversally sliced into histological sections by the usual method. The sections were subjected to HE staining, immunostaining with an anti-MyoD antibody and immunostaining with an anti-myogenin antibody. The anti-MyoD antibody used was an anti-mouse MyoD antibody (Abcam), and the anti-myogenin antibody used was an anti-mouse myogenin antibody (Abcam). A biotin-labeled anti-rabbit IgG antibody (DAKO) was used as a secondary antibody.

(2) Results

The area of granulation tissue formed on the cut surfaces was measured on the HE-staining specimens using the image-analysis software ImageJ (NIH, USA). The granulation tissue area ratios in the SV group and the PBS group were separately calculated using the following formula.

Granulation tissue area ratio=granulation tissue area on the administration side (pixel)/granulation tissue area on the non-administration side (pixel)

Figure 21:
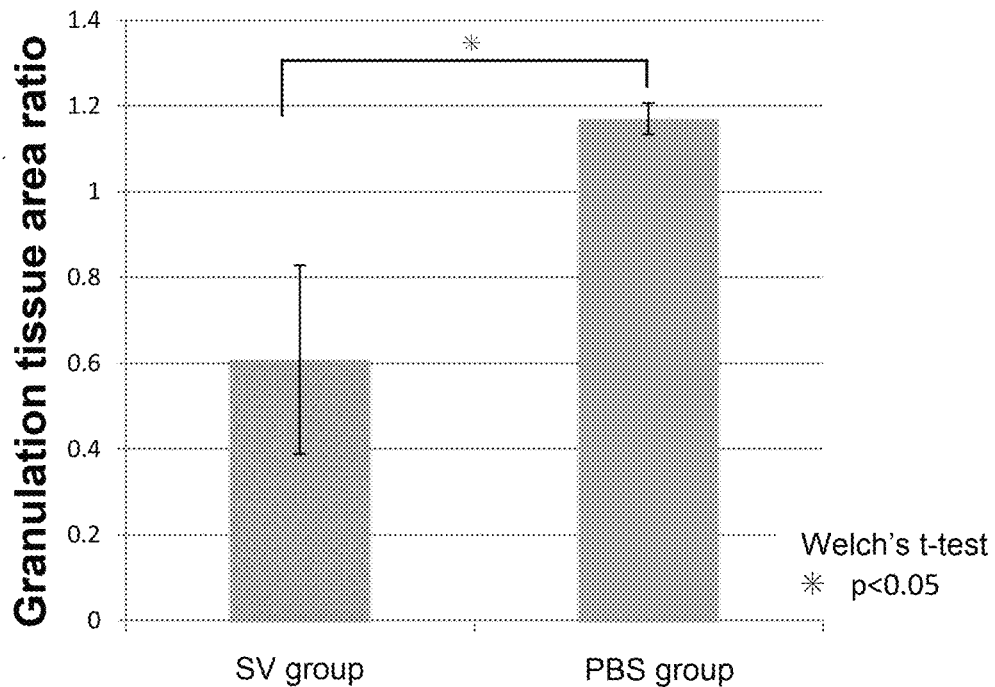
FIG. 21 shows the granulation tissue area ratio calculated after measuring the granulation tissue area at the muscle injury site on HE-staining specimens prepared by staining histological sections of masseter muscles on both sides excised at postoperative week 1 from rats subjected to incision of masseter muscles on both sides and subsequent administration of the SV peptide into the incised left masseter muscle without administration into the incised right masseter muscle (SV group) and from rats subjected to incision of masseter muscles on both sides and subsequent administration of PBS into the incised left masseter muscle without administration into the incised right masseter muscle (PBS group).

The results are shown in FIG. 21. The SV group showed a significant reduction in granulation tissue formation, while the PBS group showed no reduction in granulation tissue formation.

Images of the MyoD-immunostained specimens were taken with a digital camera mounted on a microscope, and the number of MyoD-positive nuclei in the muscle tissue area extending 2.5 mm on each side of the muscle incision site was counted. The MyoD-positive ratios in the SV group and the PBS group were separately calculated using the following formula.

Figure 22:
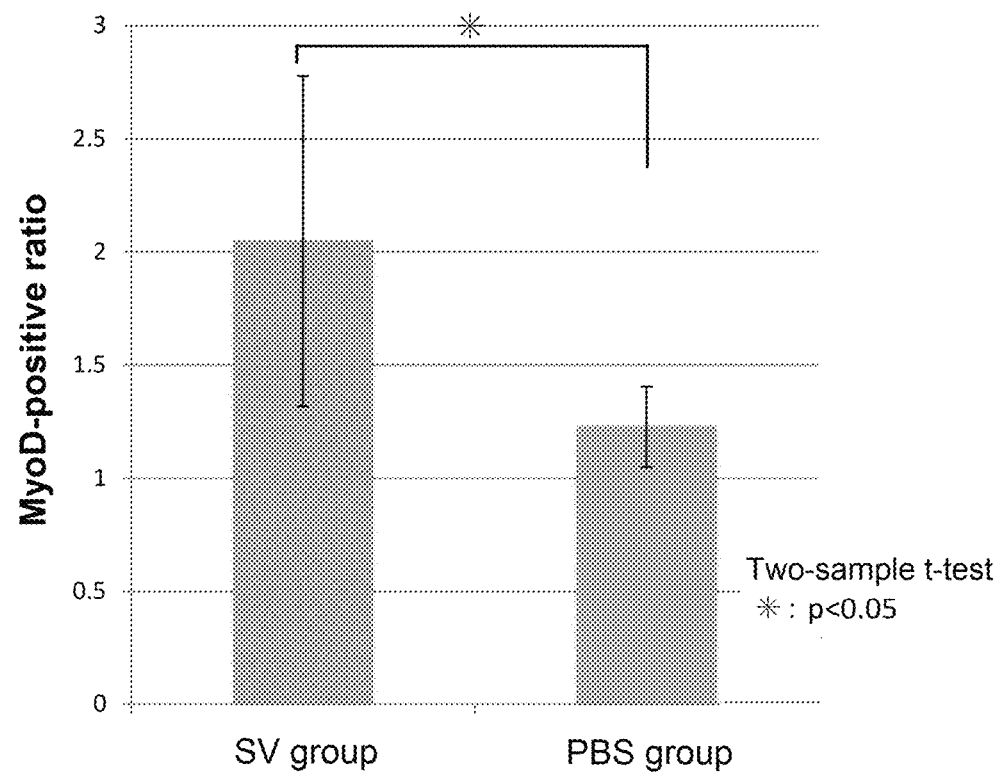
FIG. 22 shows the MyoD-positive ratio calculated after measuring the number of MyoD-positive nuclei on MyoD-immunostained specimens prepared by staining histological sections of masseter muscles on both sides excised at postoperative week 1 from rats subjected to incision of masseter muscles on both sides and subsequent administration of the SV peptide into the incised left masseter muscle without administration into the incised right masseter muscle (SV group) and from rats subjected to incision of masseter muscles on both sides and subsequent administration of PBS into the incised left masseter muscle without administration into the incised right masseter muscle (PBS group).

MyoD-positive ratio=number of MyoD-positive nuclei on the administration side/number of MyoD-positive nuclei on the non-administration side The results are shown in FIG. 22. The SV group showed a significant increase of MyoD-positive cells as compared with the PBS group.

Images of the myogenin-immunostained specimens were taken with a digital camera mounted on a microscope, and the number of myogenin-positive nuclei in the muscle tissue area extending 2.5 mm on each side of the muscle incision site was counted. The myogenin-positive ratios in the SV group and the PBS group were separately calculated using the following formula.

Figure 23:
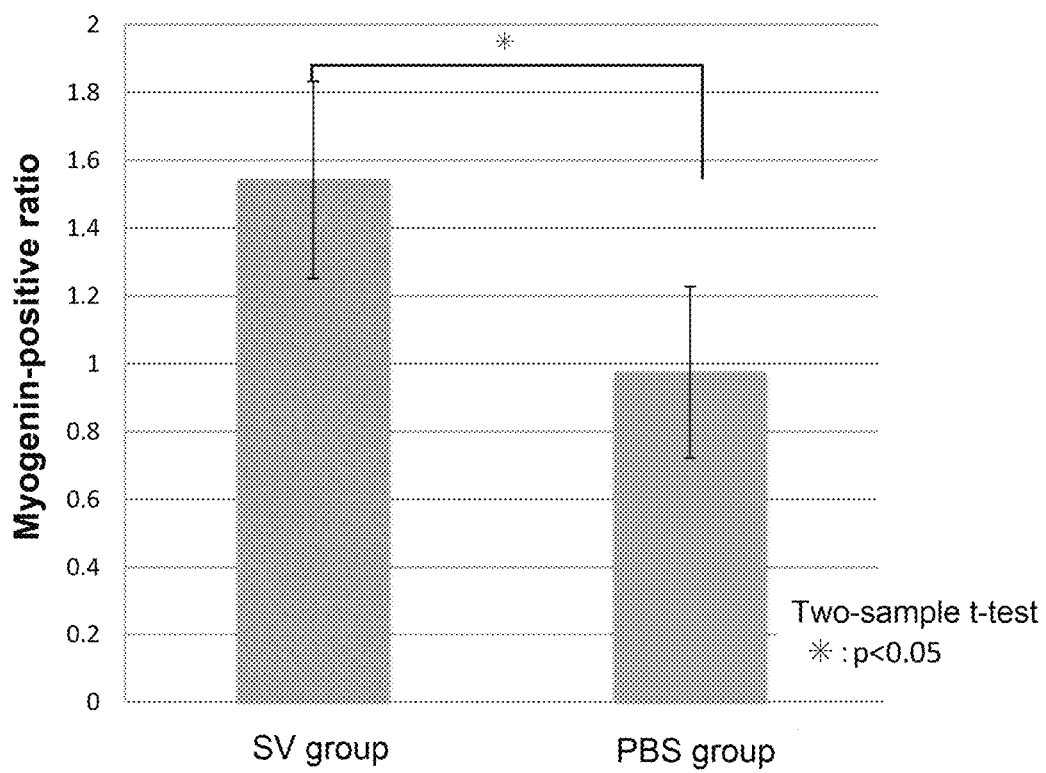
FIG. 23 shows the myogenin-positive ratio calculated after measuring the number of myogenin-positive nuclei on myogenin-immunostained specimens prepared by staining histological sections of masseter muscles on both sides excised at postoperative week 1 from rats subjected to incision of masseter muscles on both sides and subsequent administration of the SV peptide into the incised left masseter muscle without administration into the incised right masseter muscle (SV group) and from rats subjected to incision of masseter muscles on both sides and subsequent administration of PBS into the incised left masseter muscle without administration into the incised right masseter muscle (PBS group).

Myogenin-positive ratio=number of myogenin-positive nuclei on the administration side/number of myogenin-positive nuclei on the non-administration side The results are shown in FIG. 23. The SV group showed a significant increase of myogenin-positive cells as compared with the PBS group.

The above results confirmed that the SV peptide promotes differentiation of satellite cells into skeletal muscle cells at a muscle injury site, resulting in promotion of injury repair. The increase of MyoD-positive cells on the SV peptide administration side at the muscle injury site as shown above indicates that the SV peptide promotes myoblast proliferation and migration to the muscle injury site. In addition, the increase of myogenin-positive cells as shown above indicates that the SV peptide promotes differentiation of myoblasts to myotube cells at the early stage after muscle injury.

The present invention is not limited to the particular embodiments and examples described above, and various modifications can be made within the scope of the appended claims. Other embodiments provided by suitably combining technical means disclosed in separate embodiments of the present invention are also within the technical scope of the present invention. All the academic publications and patent literature cited in the description are incorporated herein by reference.

The invention claimed is:

1. A method for promoting skeletal muscle injury repair, the method comprising administering at least one peptide selected from the following (1) to (3):
   (1) a peptide consisting of the amino acid sequence of SEQ ID NO: 1,
   (2) a peptide consisting of the amino acid sequence of SEQ ID NO: 2, or
   (3) a peptide consisting of the amino acid sequence of SEQ ID NO: 3, or a salt thereof to a mammal having skeletal muscle injury.

2. The method for promoting skeletal muscle injury repair according to claim 1, wherein the method is capable of promoting satellite cell activation and/or differentiation.

3. The method for promoting skeletal muscle injury repair according to claim 1, wherein the skeletal muscle injury is muscle rupture, muscle atrophy, or muscle degeneration.

4. The method for promoting skeletal muscle injury repair according to claim 1, wherein the method is capable of reducing scar formation at a skeletal muscle injury site.

5. A method for promoting satellite cell activation and/or differentiation at a skeletal muscle injury site, the method comprising administering at least one peptide selected from the following (1) to (3):
- (1) a peptide consisting of the amino acid sequence of SEQ ID NO: 1,
- (2) a peptide consisting of the amino acid sequence of SEQ ID NO: 2, or
- (3) a peptide consisting of the amino acid sequence of SEQ ID NO: 3, or a salt thereof to a mammal having skeletal muscle injury.

6. A method for reducing scar formation at a skeletal muscle injury site, the method comprising administering at least one peptide selected from the following (1) to (3):
- (1) a peptide consisting of the amino acid sequence of SEQ ID NO: 1,
- (2) a peptide consisting of the amino acid sequence of SEQ ID NO: 2, or
- (3) a peptide consisting of the amino acid sequence of SEQ ID NO: 3, or a salt thereof to a mammal having skeletal muscle injury.

* * * * *